US009206145B2

(12) United States Patent
Dumesic et al.

(10) Patent No.: US 9,206,145 B2
(45) Date of Patent: *Dec. 8, 2015

(54) SINGLE-REACTOR PROCESS FOR PRODUCING LIQUID-PHASE ORGANIC COMPOUNDS FROM BIOMASS

(75) Inventors: James A. Dumesic, Verona, WI (US); Dante A. Simonetti, Middleton, WI (US); Edward L. Kunkes, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 474 days.

This patent is subject to a terminal disclaimer.

(21) Appl. No.: 13/289,076

(22) Filed: Nov. 4, 2011

(65) Prior Publication Data
US 2013/0116449 A1 May 9, 2013

Related U.S. Application Data

(63) Continuation of application No. 12/102,223, filed on Apr. 14, 2008, now Pat. No. 8,075,642.

(51) Int. Cl.
*C07D 307/06* (2006.01)
*C07D 309/04* (2006.01)

(52) U.S. Cl.
CPC ............ *C07D 307/06* (2013.01); *C07D 309/04* (2013.01)

(58) Field of Classification Search
CPC ... C07D 309/00; C07D 307/06; C07D 309/04
See application file for complete search history.

(56) References Cited

U.S. PATENT DOCUMENTS

| | | | |
|---|---|---|---|
| 3,845,155 A * | 10/1974 | Heckelsberg | 585/608 |
| 5,106,389 A | 4/1992 | Harandi et al. | |
| 6,953,873 B2 * | 10/2005 | Cortright et al. | 585/733 |
| 7,767,867 B2 * | 8/2010 | Cortright | 568/861 |
| 8,075,642 B2 * | 12/2011 | Dumesic et al. | 44/308 |
| 2007/0043245 A1 * | 2/2007 | Kaizik et al. | 568/857 |
| 2007/0173654 A1 | 7/2007 | Holladay et al. | |
| 2008/0216391 A1 | 9/2008 | Cortright et al. | |
| 2008/0300434 A1 | 12/2008 | Cortright et al. | |
| 2008/0300435 A1 | 12/2008 | Cortright et al. | |

FOREIGN PATENT DOCUMENTS

| | | |
|---|---|---|
| DE | 10 2007 004 351 A1 | 7/2008 |
| WO | WO 2007/103858 A2 | 9/2007 |
| WO | WO 2007/146636 A1 | 12/2007 |
| WO | WO 2009/029541 A | 3/2009 |

OTHER PUBLICATIONS

Alcala et al., "DFT studies for cleavage of C—C and C—O bonds in surface species derived from ethanol on Pt(111)," *J. Catal.* 218, 178-190 (2003).

Braca, G. et al., "Anionic ruthenium iodocarbonyl complexes as selective dehydroxylation catalysts in aqueous solution," Journal of Organometallic Chemistry, 417 (1991) 41-49, Elsevier Sequoia S.A.
Chang et al., "Conversion of Methanol and Other P-Compounds to Hydrocarbons over Zeolite Catalysts," *J. Catal.* 47, 249-259 (1977).
Chheda J. N. et al., "An overview of dehydration, aldol-condensation and hydrogenation processes for production of liquid alkanes from biomass-derived carbohydrates," Catalysis Today, 123 (2007) 59-70, Elsevier B.V.
Di Cosimo et al., "One-step MBIK synthesis: A new process for 2-propanol," *J. Catal.* 208, 114-123 (2002).
Gayubo et al., "Transformation of oxygenate components of biomass pyrolysis oil on a HZSM-5 zeolite. I. Alcohols and phenols," *Ind. Eng. Chem. Res.* 43, 2610-2618 (2004).
Gayubo et al., "Transformation of oxygenate components of biomass pyrolysis oil on a HZSM-5 zeolite. H. Aldehydes, ketones, and acids," Ind. Eng. Chem. Res. 43, 2619-2626 (2004).
Greeley & Mavrikakis, "Near-SURFACE alloys for hydrogen fuel cell applications," *Catal. Today* 111, 52-58 (2005).
Hamelinck et al., "Production of FT transportation fuels from biomass; technical options, process analysis and optimisation, and development potential," *Energy* 29, 1743-1771 (2004).
Klass, "Biomass for Renewable Energy, Fuels, and Chemicals," Academic Press, San Diego (1998).
Mehdi, Has an et al., "Dehydration and hydrogenation of carbohydrates with aqueous biphase catalysts," Database CA [Online] Chemical Abstracts Service, Columbus, Ohio, US, XP002548415 retrieved from STN Database accession No. 2004:222141 abstract and Abstracts of Papers, 227th ACS National Meeting, Anaheim, CA, US, Mar. 28-Apr. 1, 2004, Cell-095 Publisher: American Chemical Society, Washington, DC Coden: 69FGKM, 2004.
Mhadeshwar & Vlachos, "Microkinetic modeling for water-promoted CO oxidation, water-gas shift, and preferential oxidation of CO on Pt," *J. Phys. Chem. B* 108, 15246-15258 (2004).
Nikolopoulos et al., "Acetone condensation and selective hydrogenation to MIBK on Pd and Pt hydrotaclite-derived Mg—Al mixed oxide catalysts," *Appl. Catal. A—Gen.* 296, 128-136 (2005).
Pallassana & Neurock, "Reaction paths in the hydrogenolysis of acetic acid to ethanol over Pd(111), Re(0001), and PdRe alloys," *J. Catal.* 209, 289-305 (2002).

(Continued)

*Primary Examiner* — Sun Jae Yoo
(74) *Attorney, Agent, or Firm* — Joseph T. Leone, Esq.; DeWitt Ross & Stevens S.C.

(57) ABSTRACT

Disclosed is a method for preparing liquid fuel and chemical intermediates from biomass-derived oxygenated hydrocarbons. The method includes the steps of reacting in a single reactor an aqueous solution of a biomass-derived, water-soluble oxygenated hydrocarbon reactant, in the presence of a catalyst comprising a metal selected from the group consisting of Cr, Mn, Fe, Co, Ni, Cu, Mo, Tc, Ru, Rh, Pd, Ag, W, Re, Os, Ir, Pt, and Au, at a temperature, and a pressure, and for a time sufficient to yield a self-separating, three-phase product stream comprising a vapor phase, an organic phase containing linear and/or cyclic mono-oxygenated hydrocarbons, and an aqueous phase.

7 Claims, 9 Drawing Sheets

(56) References Cited

OTHER PUBLICATIONS

Perlack et al., 1-78, United States Department of Energy, Oak Ridge National Laboratory (2005).

Phatak et al., "Kinetics of the water-gas shift reaction on Pt catalysts supported on alumina and ceria," *Catal. Today* 123, 224-234 (2007).

Rollman & Valyocsik, "Zeolite Molecular Sieves," *Inorganic Syntheses*, 22:61-68 (1983).

Sato et al., "Mechanistic study of water-gas-shift reaction over $TiO_2$ supported Pt—Re and Pd—Re catalysts," *Appl. Catal. A—Gen.* 296, 80-89 (2005).

Soares et al., "Glycerol as a Source for Fuels and Chemicals by Low-Temperature Catalytic Processing," *Agnew. Chem. Int. Ed.* 45, 3982-3985 (2006).

Tyrlik, S. K. et al., "Concentrated water solutions of salts as solvents for reaction of carbohydrates. Part 2. Influence of some magnesium salts and some ruthenium species on catalysts of dehydration of glucose," Journal of Molecular Catalysis A: Chemical, 106(3) (1996), 223-33, Elsevier Science B.V.

Zhang et al., "Mixed-metal Pt monolayer electrocatalysts for enhanced oxygen reduction kinetics," *J. Am. Chem. Soc.* 127, 12480-12481 (2005).

\* cited by examiner

FIG. 6A
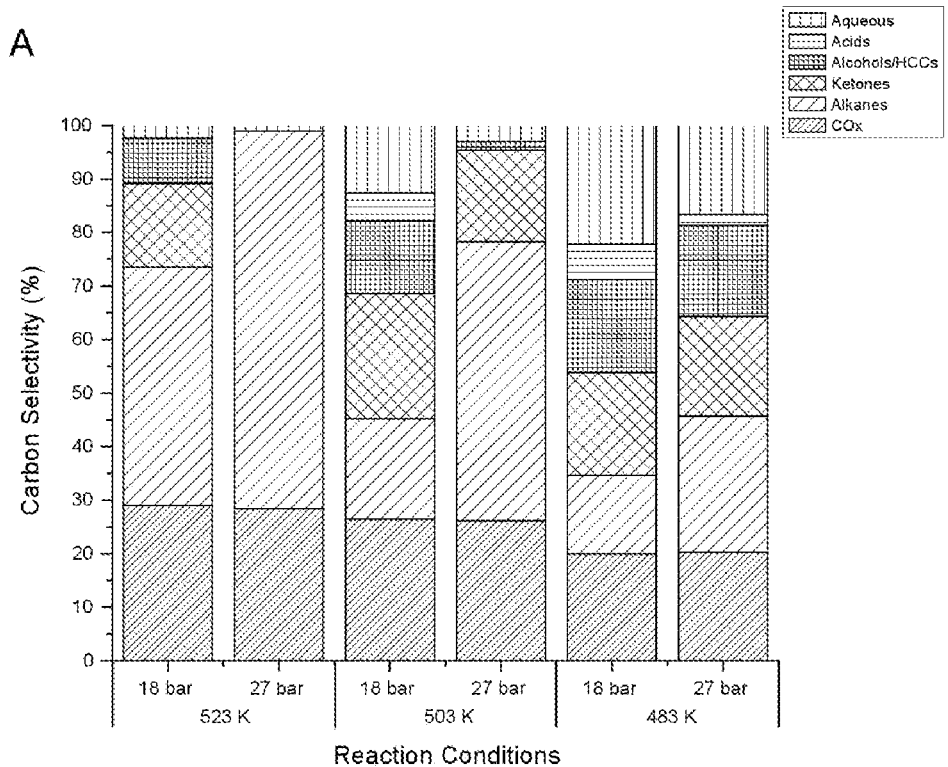
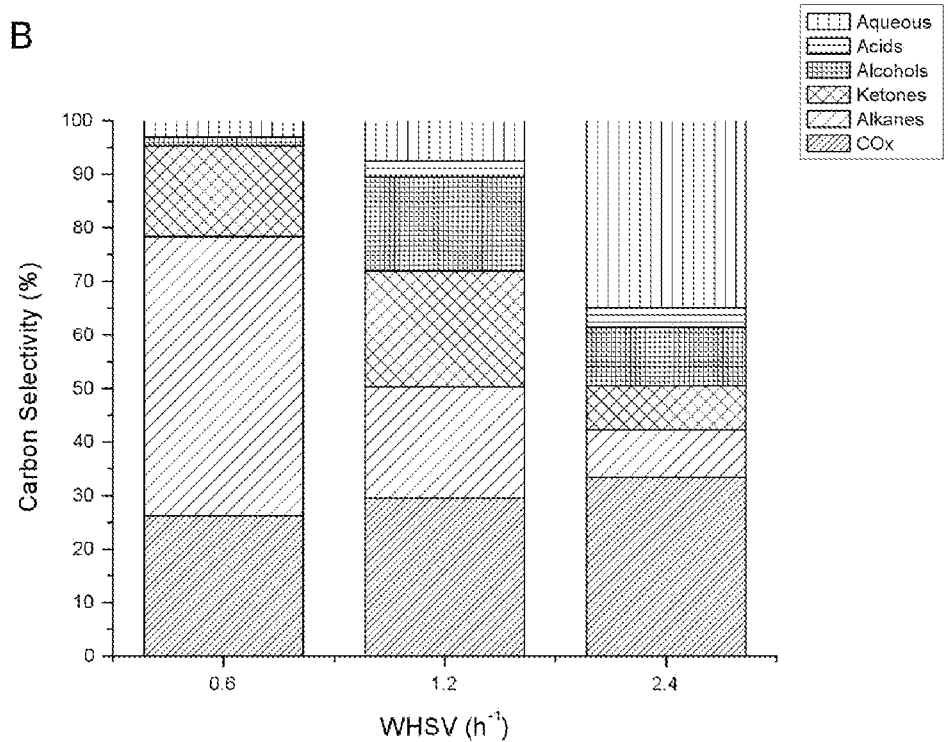
FIG. 6B

FIG. 9A
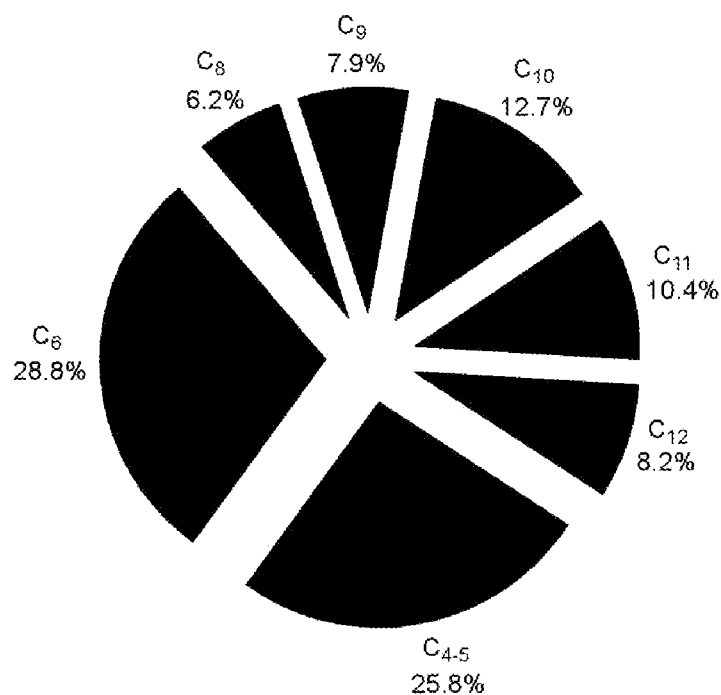
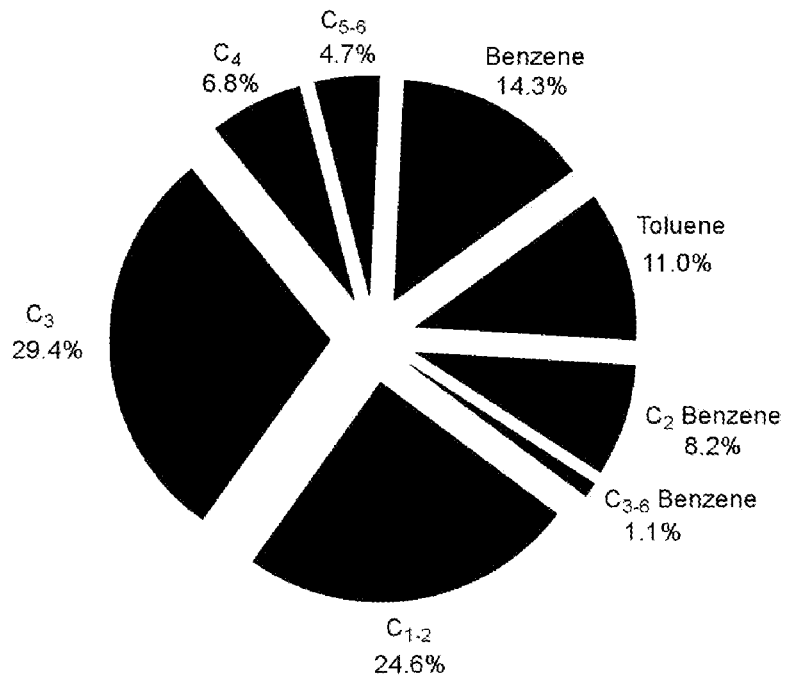
FIG. 9B

SINGLE-REACTOR PROCESS FOR PRODUCING LIQUID-PHASE ORGANIC COMPOUNDS FROM BIOMASS

CROSS-REFERENCE TO RELATED APPLICATIONS

This is a continuation of co-pending application Ser. No. 12/102,223, filed Apr. 14, 2008.

FEDERAL FUNDING STATEMENT

This invention was made with government support under DE-FG02-84ER13183 awarded by the US Department of Energy. The government has certain rights in the invention.

FIELD OF THE INVENTION

The invention is directed to a process for producing liquid-phase organic compounds via catalytic processing of aqueous-phase biomass.

BACKGROUND

Conventional transportation requires fuels that burn cleanly and that have high energy densities for efficient storage at ambient conditions. These criteria are currently met by petroleum-derived, liquid fuels (e.g., gasoline, diesel, kerosene). Petroleum is a non-renewable resource in diminishing supply, with large quantities of the known supply located in politically unstable regions of the world. Additionally, the combustion of fossil fuels to generate kinetic energy leads to emission of $CO_2$. Carbon dioxide is a greenhouse gas that contributes to global warming. See Klass, "Biomass for Renewable Energy, Fuels, and Chemicals," Academic Press, San Diego, 1998. The ecological, economical, and political issues associated with the continued reliance on petroleum-based fuels would be ameliorated (at least in part) by producing clean-burning liquid fuels from renewable biomass resources. There is a general consensus in the scientific community that the amount of biomass that could be grown globally on a sustainable basis is comparable to the annual world-wide consumption of energy by the transportation sector. Perlack et al. 1-78, United States Department of Energy, Oak Ridge National Laboratory, 2005.

The cost of transportation fuels produced from ligno-cellulosic biomass, however, is currently not competitive with the cost of fuels derived from petroleum. This is due primarily to the high costs associated with the processing of biomass to produce the fuel, rather than the cost of the biomass feedstock itself. See Hamelinck et al., "Production of FT transportation fuels from biomass; technical options, process analysis and optimisation, and development potential," Energy 29, 1743-1771 (2004). Accordingly, it is imperative to develop new processes for converting biomass to liquid fuels that involve a limited number of processing steps. Limiting the number of processing steps decreases the capital and operating expenses associated with conventional processes that require multiple reactors and separation/purification steps between reactors.

SUMMARY OF THE INVENTION

The invention described herein is an economically viable process for converting biomass to liquid alkane fuels and/or other valuable commodity chemicals. In one version of the invention, carbohydrates from biomass are converted to liquid alkanes via a cascade approach using a limited number of catalytic reactors or beds (preferably two), without the need for complex separation and/or purification steps between catalysts. Importantly, the liquid alkane products produced by this version of the invention can be processed and distributed by existing petrochemical technologies and infrastructure. These products can also be used in existing transportation vehicles utilizing internal combustion engines.

In another version of the invention, the same approach is utilized to produce mono-functional compounds that are commodity or fine chemical products that can be used in any number of conventional chemical applications. Thus, the invention is a platform technology for producing liquid fuels for the high-volume transportation market, and for producing chemical intermediates for the lower-volume, but higher-value, chemicals and polymers markets.

In the present invention, carbohydrates, which are the predominate class of compounds in ligno-cellulosic biomass, are converted to mono-functional chemical intermediates, which are currently derived almost exclusively from fossil fuels. According to the present invention, these mono-functional chemical intermediate can then be converted to higher molecular weight alkanes (e.g., $C_5$-$C_{12}$ for gasoline, $C_9$-$C_{16}$ for jet fuel, and $C_{10}$-$C_{20}$ for diesel applications). As shown in FIG. 1, the inventors have found, according to the invention, that the predominant intermediates produced by catalytic processing of sorbitol (60 wt % in water) over a Pt—Re/C catalyst at temperatures near 500 K are alcohols, ketones, carboxylic acids, and alkanes containing 4, 5, or 6 carbon atoms, as well as heterocyclic tetrahydrofuran and tetrahydropyran compounds. The liquid effluent from the Pt—Re/C catalyst separates spontaneously at room temperature into an organic phase containing the aforementioned compounds and an aqueous phase containing more highly oxygenated organic compounds (e.g., diols, isosorbide [systematic name: 2,6-dioxabicyclo[3.3.0]octan-4-ol], and the like). The organic liquid derived from sorbitol can then be upgraded, in one version of the invention, to liquid fuel components by aldol-condensation and hydrogenation reactions over a catalyst (preferably a bi-functional $CuMg_{10}Al_7O_x$ catalyst) to form a stream of $C_4$-$C_{12}$ compounds. (See, for example, Di Cosimo et al., "One-step MIBK synthesis: A new process from 2-propanol," J. Catal. 208, 114-123 (2002) and Nikolopoulos et al., "Acetone condensation and selective hydrogenation to MIBK on Pd and Pt hydrotalcite-derived Mg—Al mixed oxide catalysts," Appl. Catal. A-Gen. 296, 128-136 (2005).) Alternatively, the organic liquid derived from sorbitol can be upgraded by alkylation and hydride transfer reactions over a catalyst to form olefins, alkanes, and aromatics. See, for example, Chang et al., "Conversion of Methanol and Other O-Compounds to Hydrocarbons over Zeolite Catalysts," J. Catal. 47, 249-259 (1977); Gayubo et al., "Transformation of oxygenate components of biomass pyrolysis oil on a HZSM-5 zeolite. I. Alcohols and phenols," Ind. Eng. Chem. Res. 43, 2610-2618 (2004); and Gayubo et al., "Transformation of oxygenate components of biomass pyrolysis oil on a HZSM-5 zeolite. H. Aldehydes, ketones, and acids," Ind. Eng. Chem. Res. 43, 2619-2626 (2004).

The organic liquid derived from sorbitol also serves as a platform for organic chemical intermediates that can be used as blending agents in transportation fuels, olefins for the polymer industry, or used as solvents. A key advantage of the present invention is that it removes more than 80% of the oxygen contained in the feedstock reactant in the first reaction step. This allows the subsequent upgrading processes (e.g., condensation and/or distillation) to operate at reduced capacity and with increased efficiency.

Thus, a first version of the invention is directed to a method for preparing liquid fuel and chemical intermediates from biomass-derived oxygenated hydrocarbons. Here, the method comprises reacting in a single reactor an aqueous solution of a biomass-derived, water-soluble oxygenated hydrocarbon reactant, in the presence of a catalyst comprising a metal selected from the group consisting of Cr, Mn, Fe, Co, Ni, Cu, Mo, Tc, Ru, Rh, Pd, Ag, W, Re, Os, Ir, Pt, and Au, at a temperature, and a pressure, and for a time sufficient to yield a self-separating, three-phase product stream. The three-phase product stream comprises a vapor phase, an organic phase comprising linear or cyclic mono-oxygenated hydrocarbons, and an aqueous phase.

In another version of the invention, the organic phase produced as described in the preceding paragraph is subjected to a carbon-carbon bond-forming reaction, in the presence of a metal-containing catalyst, to yield $C_8$-$C_{12}$ compounds. Another version of the invention further comprises subjecting the $C_8$-$C_{12}$ compounds so formed to a hydrodeoxygenation reaction to yield $C_8$-$C_{12}$ alkanes.

In yet another version of the invention, the organic phase produced as described in the first version of the invention is subjected to an aldol condensation reaction to yield compounds having more carbon atoms than the reactant. This step can also be followed by a hydrodeoxygenation reaction to yield alkanes.

In still another version of the invention, the organic phase produced as described in the first version of the invention is hydrogenated, wherein ketones present in the organic phase are reduced to alcohols. The alcohols are then dehydrated to yield alkenes. The alkenes so formed may optionally be subjected to an alkylation reaction over an acid catalyst to form carbon-carbon bonds, thereby yielding longer chain alkenes.

In yet another version of the invention, the organic phase produced as described in the first version of the invention is hydrogenated, wherein ketones present in the organic phase are reduced to alcohols, and the alcohols are then optionally converted to aromatic compounds over an acid catalyst, thereby yielding alkylated aromatic compounds for solvent and gasoline applications.

It is preferred that the catalyst comprises platinum, or a combination of platinum and rhenium. Optionally, the catalyst may further comprise a reducible metal oxide selected from the group consisting of oxides of one or more of the following metals: Ti, V, Cr, Mn, Fe, Co, Nb, Mo, Sn, Sb, Te, W, Pb, Bi, Ce, and Eu.

It is generally preferred that the catalyst is disposed on a support. Preferred supports are selected from the group consisting of silica, alumina, zirconia, titania, ceria, vanadia, carbon, heteropolyacids, silica-alumina, silica nitride, boron nitride, and mixtures thereof. The support may be zeolites, nanoporous carbon, nanotubes, and/or fullerenes. The method may further comprise a step wherein the support is treated with an acid or a base, whereby surface chemistry of the support is modified to alter its acidic or basic properties.

In the preferred versions, the method comprises reacting the aqueous solution at a temperature of from about 400 K to about 1000 K, at a pressure of from atmospheric to about 50 bar, and over a catalyst, wherein the organic phase yielded by the reaction comprises compounds having from 4 to 6 carbon atoms and selected from the group consisting of alcohols, ketones, carboxylic acids, and 5- and 6-membered oxygen-containing heterocycles.

The catalysts to be used in the present invention preferably comprise one or more metals falling within Groups 6 through 11 and Periods 4 through 6 of the periodic table. Thus, the catalyst preferably comprises one or more metals selected from the group consisting of Cr, Mn, Fe, Co, Ni, Cu, Mo, Tc, Ru, Rh, Pd, Ag, W, Re, Os, Ir, Pt, and Au. The catalyst may be mixtures thereof and/or alloys thereof and/or mixtures or alloys of one of the listed metals with other metals.

Another possibility for catalyst selection is to combine one of the aforementioned metals with a reducible metal oxide, such as titania, ceria, or vanadia. In this scenario, the role of the reducible metal oxide is to facilitate cleavage of C—O bonds in the biomass-derived oxygenated hydrocarbon reactants. It is believed that the mechanism for this effect is related to the ability of the reducible metal oxide to provide reactive oxygen or hydroxyl groups that react with oxygenated hydrocarbon species by dehydration reactions.

It is also much preferred that the catalyst be adhered to a support, such as silica, alumina, zirconia, titania, ceria, vanadia, carbon, heteropolyacids, silica-alumina, silica nitride, boron nitride, and mixtures thereof. The active metals may be adhered to a nanoporous support, such as zeolites, nanoporous carbon, nanotubes, and fullerenes. The support itself may be surface-modified to modify surface moieties, especially surface hydrogen and hydroxyl moieties that may cause localized pH fluctuations. The support can be surface-modified by treating it with silanes, alkali compounds, alkali earth compounds, and the like. The surface chemistry of the support can also be modified by treatments that make it more acidic or basic, for example, by treating carbon supports with nitric acid or ammonia, respectively.

It is preferred, although not required, that the biomass-derived, water-soluble oxygenated hydrocarbon reactant have a carbon-to-oxygen ratio of 1:1. Particularly preferred oxygenated hydrocarbon reactants include ethanediol, ethanedione, glycerol, glyceraldehyde, aldotetroses, aldopentoses, aldohexoses, ketotetroses, ketopentoses, ketohexoses, and alditols. From among the oxygenated hydrocarbons having six carbon atoms, glucose and sorbitol are preferred. Sorbitol is most preferred. Ethanediol, glycerol, and glyceraldehyde are the preferred oxygenated hydrocarbons from among those having less than six carbon atoms. In this group of reactants, glycerol is most preferred.

The invention will function with mixed feedstocks of oxygenated hydrocarbons, that is, feedstocks containing mixtures of two or more oxygenated hydrocarbons.

A principal advantage of the subject invention is that the oxygenated hydrocarbon reactants can be produced from renewable resources, such as biomass. Thus, the present method can be used to generate a fuel source, namely hydrocarbons, as well as valuable mono-functional, oxygen-containing intermediates and solvents (ketones, alcohols, etc.) from an abundant and fully renewable source. Because living plant matter consumes carbon dioxide, the use of these feedstocks in power generation applications does not result in a net increase of carbon dioxide vented to the atmosphere.

Another advantage of the present invention is that it can be selectively optimized to yield hydrocarbons and oxygenated hydrocarbons having 4 or more carbon atoms, such as butane, pentane, hexane, butanol, pentanol, hexanol, butanone, pentanone, and hexanone, etc. or it can be selectively optimized to yield valuable oxygen-containing compounds such as substituted or unsubstituted tetrahydrofurans, tetrahydropyrans, carboxylic acids, alcohols, etc. The resulting stream, which spontaneously separates into an organic phase and an aqueous phase, can also be further manipulated, if desired. For example, the hydrocarbons can be dehydrogenated to yield olefins.

The process will work with literally any water-soluble carbohydrate, including glycerol, sorbitol, glucose, sucrose, lactose, xylose, etc. $C_3$ to $C_6$ sugar alcohols such as glycerol, erythritol, arabitol, xylitol, sorbitol, and the like are particularly preferred. These reactants can be present in concentrated aqueous solutions—up to their maximum solubilities, generally about 80 wt % in water and higher. Lower concentrations of the reactants in water may also be used if desired.

The compound produced using the present invention can be utilized in any process where a hydrocarbon or oxygenated hydrocarbon is required. Thus, the primary utility of the method recited herein is to produce conventional hydrocarbon fuels from biomass. Another utility is to produce commodity solvents such as tetrahydrofuran and tetrahydropyran. Another utility is to produce alcohols, ketones, and carboxylic acids containing 4, 5, or 6 (or more) carbon atoms. All of these utilities are accomplished using a carbohydrate feedstock derived from a renewable source, namely biomass. The vast majority of all of these compounds are conventionally fabricated from petroleum rather than renewable resources.

BRIEF DESCRIPTION OF THE DRAWINGS

FIGS. 6A and 6B are histograms for carbon selectivities for converting sorbitol over 10 wt % Pt—Re/C using: FIG. 6A: 0.04 mL min$^{-1}$ of a 60 wt % sorbitol feed and 3.0 g catalyst (WHSV=0.60 h$^{-1}$) at pressures of 18 bar and 27 bar and temperatures between 483 K and 523 K; and FIG. 6B: flow rates of 60 wt % sorbitol between 0.04-0.16 mL min$^{-1}$ (3.0 g catalyst; WHSV=0.60-2.4 h$^{-1}$) at 27 bar and 503 K.

FIGS. 9A and 9B are pie charts depicting product distributions for the upgrading of the organic liquid product from sorbitol conversion over Pt—Re/C. FIG. 9A depicts condensation to $C_8$-$C_{12}$ species over $CuMg_{10}Al_7O_x$ at 573 K and 5 bar. FIG. 9B depicts upgrading to olefins and aromatic species over H-ZSM-5 at 673 K and atmospheric pressure. In both figures, $C_R$ represents species containing x carbon atoms. $C_{1-2}$ represents $CO_2$, $CH_4$, $C_2H_4$, and $C_2H_6$. $C_x$ Benzene represents benzene rings functionalized with x total carbon groups (e.g., ethyl and methyl).

DETAILED DESCRIPTION

The following abbreviations and definitions are used throughout the specification and claims. Claims not explicitly defined herein are to be given their accepted definitions within the field of chemistry and/or chemical engineering.

"Alkane/alkyl"=linear, branched, or cyclic, saturated hydrocarbons, preferably having from 1 to 24 carbon atoms. "Lower alkane/alkyl," generally refers to alkanes having from 1 to 4 carbon atoms.

"Alkene/alkenyl"=linear, branched, or cyclic, unsaturated hydrocarbons (including aromatic hydrocarbons), preferably having from 2 to 24 carbon atoms.

"Biomass"=any organic matter available on a renewable basis. As used herein, "biomass" explicitly includes (without limitation) forest and mill residues, agricultural crops and wastes, wood and wood wastes, grasses, non-crop plant matter, animal wastes, livestock operation residues, aquatic plants, trees and plants, and municipal and industrial wastes.

"Biomass-derived"=compounds or compositions fabricated or purified from biomass.

"GHSV"=gas hourly space velocity.

"Heteropolyacid"=a class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (−3) charge, and thus requires three cations to satisfy electro-neutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"psig"=pounds per square inch relative to atmospheric pressure (i.e., gauge pressure).

"Space Velocity"=the mass/volume of reactant per unit of catalyst per unit of time.

"WHSV"=weight hourly space velocity=mass of oxygenated compound per mass of catalyst per h.

"WGS"=water-gas shift.

Figure 1:
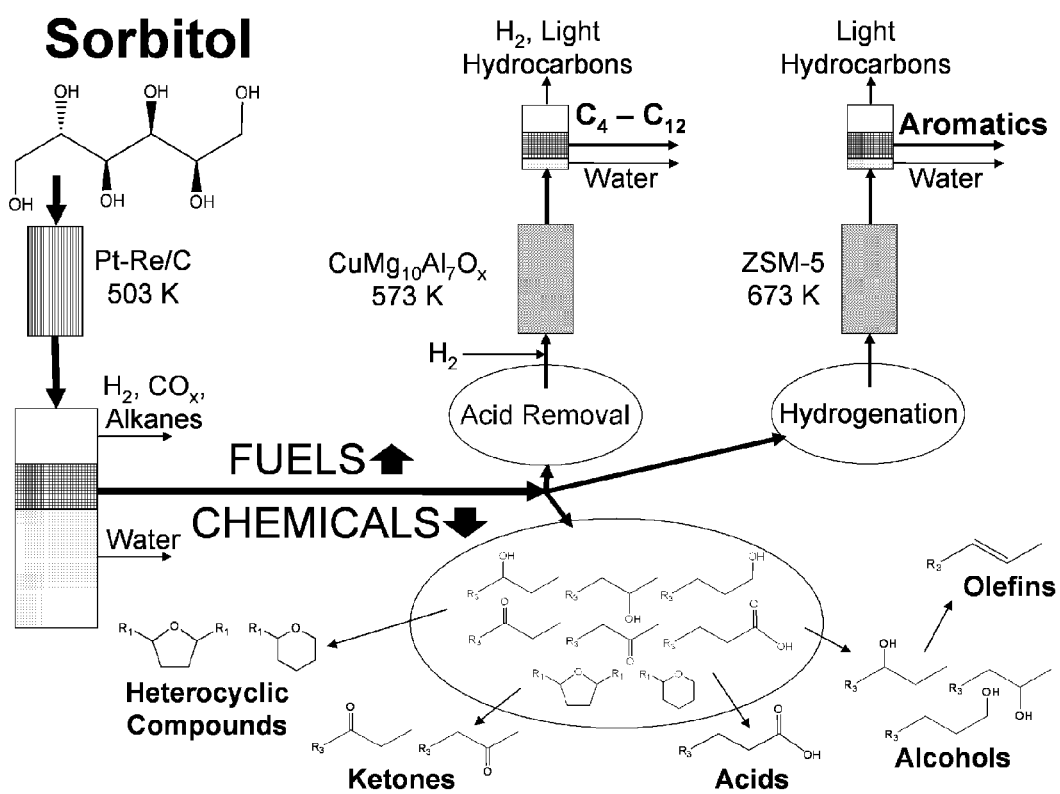
FIG. 1 is a schematic representation of one version of the invention for producing mono-functional organic compounds from catalytic processing of sorbitol. This version of the invention provides a platform for producing fuels and chemicals. In the figure, $R_3$ represents alkyl, preferably lower alkyl (and most preferably $CH_3$, $CH_3CH_2$ or $CH_3CH_2CH_2$ groups), and $R_1$ represents H or alkyl or lower alkyl (preferably $CH_3$).

I. Overview and General Considerations:

FIG. 1 presents a schematic diagram of a preferred version of the present invention. Moving left-to-right through FIG. 1, a water-soluble, oxygenated hydrocarbon derived from biomass is used as the reactant. This is exemplified by sorbitol in FIG. 1. An aqueous solution of the reactant is reformed at elevated temperature and at pressures and times, over a metal-containing catalyst, to yield a three-phase product stream: a vapor phase, an organic phase, and an aqueous phase. The vapor phase generally contains hydrogen and carbon dioxide, and may also contain lower alkanes. The organic phase contains oxygenated compounds, including alcohols, ketones, carboxylic acids, and oxygen-containing heterocycles. The aqueous phase contains water-soluble compounds, such as polyols and the like. Of particular utility and advantage in the present invention is that the organic phase and the aqueous phase spontaneously separate, thus greatly simplifying downstream processing of the product mixture. Thus, the effluent from the reactor can be separated based on vapor pressure and solubility essentially automatically—the vapors are tapped off the product stream and the organic and aqueous phases separate spontaneously, as shown in the left-hand side of FIG. 1. If desired, the resulting compounds can then be further processed to yield high molecular-weight fuels, aromatics, olefins, etc.

Figure 2:
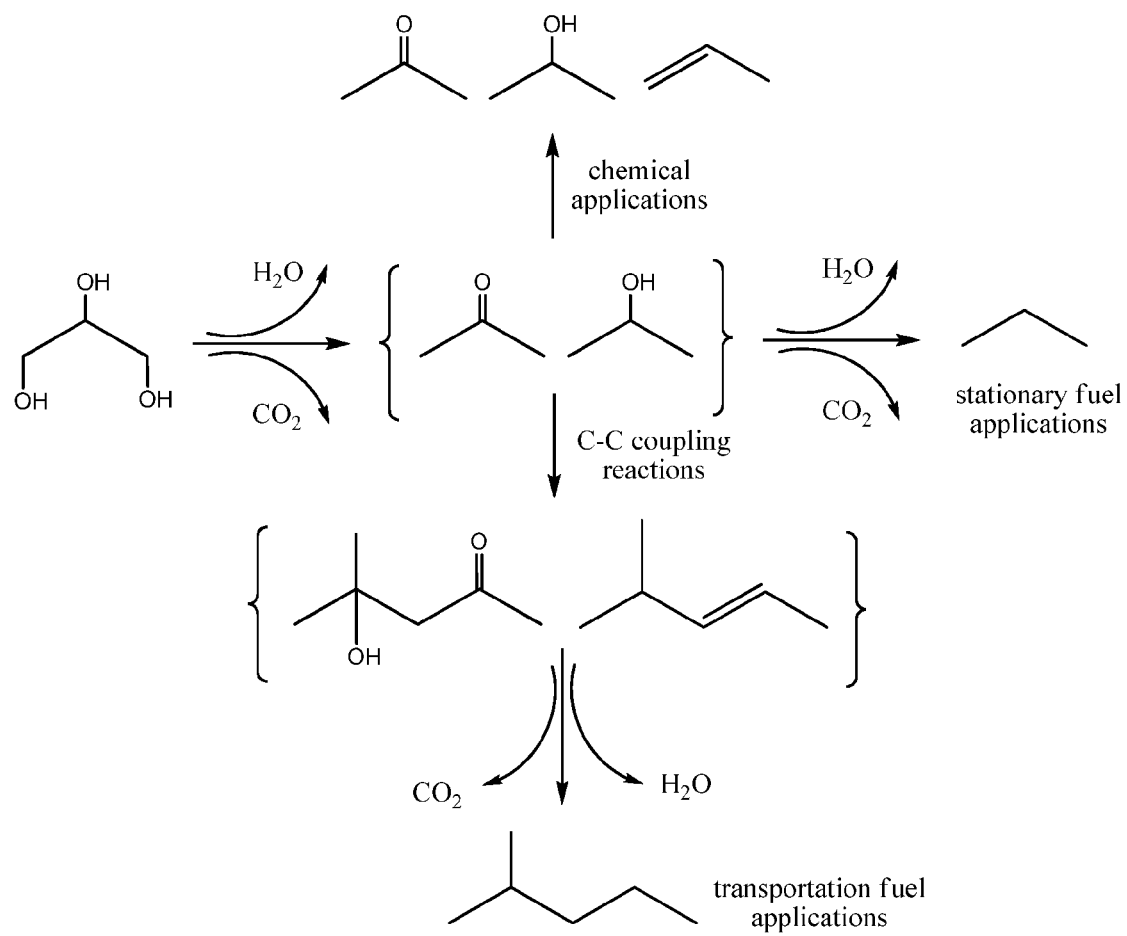
FIG. 2 is a schematic representation of another version of the invention wherein glycerol is converted to ketones and alcohols. These products are useful as intermediates for chemical applications, for conversion to lower alkanes for stationary fuel applications, or as a feedstock for C—C coupling reactions followed by conversion to higher molecular weight alkanes for transportation fuels. The production of $CO_2$ is caused by the coupling of reduction reactions with aqueous-phase reforming.

FIG. 2 presents a brief description of various reactions that can be accomplished using the present invention when glycerol is the reactant. As shown, using downstream C—C coupling reactions, the invention can be used to make ketones, alcohols, and or alkenes, that can then be further processed into long-chain alkanes for transportation fuel applications. See the bottom of FIG. 2. Or the raw organic phase from the product stream can be dehydrated/reduced to yield lower alkanes suitable for stationary fuel applications. See the right-hand portion of FIG. 2. Or the reaction can be optimized to yield valuable chemicals from biomass, such as acetone, 2-propanol, and propene. See the top of FIG. 2.

The metallic catalyst systems preferred for use in the present invention comprise one or more metals from within Groups 6 through 11 and Periods 4 through 6 of the periodic table. Catalysts for use in the invention thus preferably comprise one or more metals selected from the group consisting of Cr, Mn, Fe, Co, Ni, Cu, Mo, Tc, Ru, Rh, Pd, Ag, W, Re, Os, Ir, Pt, and Au, alloys thereof, and mixtures thereof, preferably (although not necessarily) adhered to a support. From among these metals, the most preferred are platinum and rhenium.

Another possibility for catalyst selection is to combine one of the aforementioned metals with a reducible metal oxide, such as titania, ceria, or vanadia. In this scenario, the role of the reducible metal oxide is to facilitate cleavage of C—O bonds in the biomass-derived oxygenated hydrocarbon reactants. For example, a —C—OH group in an oxygenated hydrocarbon can react with a M-OH group of a reducible metal (M) oxide, to form water, thereby breaking the C—OH bond and forming an M=O species. As an example, a catalyst can be formulated by depositing Pt and vanadia on a support such as titania.

The metallic catalyst may also be combined or used in conjunction with (or in series with) additional catalysts, notably ZSM-5-type catalysts, as described in U.S. Pat. No. 3,702,886, issued Nov. 14, 1972, to Argauer & Landolt. ZSM-5-type catalysts (from the working compound name Zeolite Socony Mobil #5), are a genus of medium pore zeolites with channels defined by ten-membered rings. They are aluminosilicate zeolites with high silica contents and low aluminum contents. Their structure is based on channels with intersecting tunnels. The aluminum sites are very acidic. The substitution of $Al^{3+}$ in place of the tetrahedral $Si^{4+}$ silica requires the presence of an added positive charge. When this charge is provided by $H^+$ (i.e., H-ZSM-5), the zeolite is very acidic. ZSM-5-type catalysts are available commercially and can be fabricated as per U.S. Pat. No. 3,702,886, as well as according to Rollman & Valyocsik, "Zeolite Molecular Sieves," *Inorganic Syntheses,* 22:61-68 (1983).

If loaded onto a support, the metallic catalyst should be present in an amount of from about 0.25% to about 50% by total weight of the catalyst system (the weight of the support being included), with an amount of from about 1% to 30% by total weight being preferred. It is preferred that a support be used. The support should be one that provides a stable platform for the chosen catalyst and the reaction conditions. The supports include, but are not limited to, silica, alumina, zirconia, titania, ceria, carbon, silica-alumina, silica nitride, boron nitride, vanadia, heteropolyacids, and mixtures thereof. Nanoporous supports such as zeolites, carbon nanotubes, or carbon fullerenes may be utilized. From among these supports, carbon, silica, and zeolites are preferred. Carbon black (e.g., Vulcan XC-72-brand, Cabot Corporation, Boston, Mass.) supports and peat-derived activated carbon supports (e.g., Norit SX 1-G-brand, Norit Americas, Inc., Marshall, Tex.) promote the formation of dispersed bimetallic Pt—Re nanoparticles (1-3 nm). Carbon is an inert support that will not interfere with the function of the metals dispersed on it, and therefore will not contribute significantly to detrimental reactions such as coke formation. Activated carbon-supported Pt—Re catalysts display increased stability during aqueous phase biomass processing as compared to Pt—Re supported on carbon black. The increased stability is likely a result of stronger interactions between dispersed metal crystallites and the functionalized surface of the activated carbon—leading to greater sintering resistance.

If a support is omitted, the metallic catalyst should be in a very finely powdered state, sintered, or in the form of a metallic foam. Where a support is omitted, metal foams are preferred. Metal foams are extremely porous, metallic structures that are reasonably stiff (they are sold in sheets or blocks). They are very much akin in structure to open-cell foamed polyurethane. Gas passing through a metal foam is forced through an extremely tortuous path, thus ensuring maximum contact of the reactants with the metal catalyst. Metal foams can be purchased commercially from a number of national and international suppliers, including Recemat International B.V. (Krimpen aan den Ijssel, the Netherlands), a company that markets "RECEMAT"-brand metal foam. In the United States, a very wide variety of metal foams can be obtained from Reade Advanced Materials (Providence, R.I. and Reno, Nev.).

The support may also be treated, as by surface-modification, to modify surface moieties such as hydrogen and hydroxyl groups. Surface hydrogen and hydroxyl groups can cause local pH variations that may affect catalytic efficiency. The support can be modified, for example, by treating it with a modifier selected from the group consisting sulfates, phosphates, tungstenates, and silanes. Particularly useful catalyst systems for the practice of the invention include, but are not limited to, platinum and/or rhenium supported on carbon, silica, or alumina. The most preferred catalysts comprises platinum and rhenium disposed on a carbon support. The surface chemistry of the support can also be modified by treatments that make it more acidic or basic, for example, by treating carbon supports with nitric acid or ammonia, respectively. The functional groups on the catalyst may provide for improved resistance to sintering of metal particles.

The catalyst systems used in the present invention can be prepared by conventional methods known to those in the art. These methods include evaporative impregnation techniques, incipient wetting techniques, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

The reforming method of the present invention should generally be carried out at temperatures and pressures at which the thermodynamics of the desired reactions are favorable. The pressure selected for the reactions varies with the temperature. For condensed phase liquid reactions, the pressure within the reactor must be sufficient to maintain the reactants in the condensed liquid phase. For vapor phase reactions, the present invention should be carried out at a temperature where the vapor pressure of the oxygenated hydrocarbon reactant is at least about 0.1 atm (and preferably a good deal higher), and the thermodynamics of the reactions are favorable. This temperature will vary depending upon the specific reactant(s) used, but is generally in the range of from about 400 K to 1000 K (127° C. to 727° C.), and more preferably in the range of from about 450 K to about 600 K (177° C. to 327° C.).

The reaction pressure will varying depending on the temperature and the desired product mix being optimized. Generally, reaction pressures will range from atmospheric to 50 bar, and more typically from 5 to 30 bar.

II. Forming Alkanes from Carbohydrates:

For purposes of brevity only, the primary biomass-derived reactant that is discussed in the following description is sorbitol, which can be formed in nearly 100% yield by hydrogenation of glucose. Glucose is the most abundant carbohydrate found in nature. See Klass, supra. The invention, however, will work with any carbohydrate or oxygenated hydrocarbon feedstock having two or more carbon atoms (e.g., glycerol), including, by way of example and not limitation, ethanediol, ethanedione, glycerol, glyceraldehyde, aldotetroses, aldopentoses, aldohexoses, ketotetroses, ketopentoses, ketohexoses, and alditols. From among the carbohydrates having six carbon atoms, glucose and sorbitol are the preferred reactants. Ethanediol, glycerol, and glyceraldehyde are the preferred reactants from among those having less than six carbon atoms. The invention will also function with mixed feedstocks of carbohydrates, that is, feedstocks containing mixtures of two or more distinct carbohydrates.

The catalytic conversion of glycerol is also described because converting this $C_3$-polyol according to the present invention leads to a smaller number of reaction products as compared to sorbitol, a $C_6$-polyol. Glycerol is also a desirable feedstock for other reasons: glycerol can be produced from renewable resources, such as by fermentation of glucose or as a by-product of the transesterification of triglycerides in the production of biodiesel. Soares et al., "Glycerol as a Source for Fuels and Chemicals by Low-Temperature Catalytic Processing," Angew. Chem. Int. Ed. 45, 3982-3985 (2006). The growing production of biodiesel via the transesterification of triglycerides has led to a worldwide glut of glycerol as of year 2008. Glycerol is thus a renewable, low-cost, and plentiful feedstock.

Catalytic conversions of sugars and polyols over heterogeneous catalysts are typically carried out at temperatures from about 470 to about 570 K to achieve high reaction rates (e.g., turnover frequencies near 1 s$^{-1}$) without undergoing extensive decomposition by undesirable side reactions. At these temperatures and under anaerobic conditions, the most thermodynamically favorable process (i.e., the reaction having the most negative value of $\Delta G°$) is the conversion of sugars and polyols to alkanes. Glycerol is used herein as a species representative of the genus of polyols. Thus the genus of sugars (having a stoichiometry of $C_nO_nH_{2n}$) can be represented by the species glyceraldehyde or dihydroxyacetone. The stoichiometry for converting glycerol to propane can be considered as the reduction of glycerol to propane combined with the aqueous phase reforming of glycerol to $H_2$ and $CO_2$, as given by reactions 1 (reduction) and 2 (reforming) below:

$$C_3O_3H_8 + 3H_2 \rightarrow C_3H_8 + 3H_2O \quad \Delta G° = -72 \; \Delta H = -62 \text{ kcal/mol} \qquad 1.$$

$$C_3O_3H_8 + 3H_2O \rightarrow 3CO_2 + 7H_2 \quad \Delta G° = -53 \; \Delta H = 35 \text{ kcal/mol} \qquad 2.$$

The aforementioned values of $\Delta G°$ are calculated for a reaction temperature of 520 K. The appropriate combination of reaction 1 with reaction 2 leads to reaction 3, in which the $H_2$ required for the reduction reaction is balanced with $H_2$ produced by the reforming reaction:

$$3. \; C_3O_3H_8 \rightarrow \frac{7}{10}C_3H_8 + \frac{9}{10}CO_2 + \frac{6}{5}H_2O$$

$$\Delta G° = -67$$

$$\Delta H = -33 \text{ kcal/mol}$$

Converting glycerol to propane is necessarily accompanied by the production of $CO_2$ according to reaction 3 because $H_2$ and $CO_2$ are produced in the reforming reaction (reaction 2) that supplies $H_2$ for the reduction reaction (reaction 1).

Converting glycerol to propane according to reaction 3 is an exothermic process in which 91% of the heating value of the glycerol reactant is retained in the propane product. See Soares et al., supra. While lower alkanes, such as propane, have value as fuels for stationary applications (e.g., heating homes), it is desirable to produce heavier alkanes as fuels for transportation applications, such as $C_6$-$C_{12}$ for gasoline, $C_9$-$C_{16}$ for jet fuel, and $C_{10}$-$C_{22}$ diesel applications. But converting propane to heavier alkanes, such as hexane, is not thermodynamically favorable at temperatures near 520 K, as dictated by reaction 4 below:

$$2C_3H_8 \rightarrow C_6H_{14} + H_2 \quad \Delta G° = 14 \; \Delta H = 9 \text{ kcal/mol} \qquad 4.$$

Accordingly, once an alkane is produced from a sugar or a polyol, it is not thermodynamically favorable to increase the molecular weight of this alkane at typical reaction temperatures. Thus, when the goal of catalytic processing is to produce alkanes containing a larger number of carbon atoms than are present in the initial sugar or polyol reactant, under thermodynamically favorable conditions, then C—C coupling reactions must be employed prior to removing all of the oxygen atoms and saturating all of the double bonds in the reactant molecule.

III. Reaction Intermediates and Pathways:

Converting a polyol, such as glycerol, to alkanes takes place through the formation of a variety of chemical intermediates, such as alcohols and ketones. As illustrated schematically in FIG. 2, these mono-oxygenated compounds and alkenes (e.g., acetone, 2-propanol, propene, etc., shown at the top of FIG. 2) are commodity chemicals and can be used for various chemical applications, e.g., alcohols can be dehydrated to olefins for the polymer industry, etc. The further removal of oxygen from these intermediates leads to the formation of light alkanes (i.e., propane in the case of glycerol) that have use as fuels for stationary applications. To produce alkanes having higher molecular weights for use as transportation fuels, C—C coupling reactions can be carried out utilizing C=O and/or C=C double bonds in reaction intermediates formed by partial removal of oxygen atoms from glycerol, followed by further removal of oxygen atoms to produce the final alkane product. Possible routes for C—C coupling reactions between reaction intermediates include aldol-condensation reactions between molecules containing C=O double bonds over basic or acid catalysts, and alkylation reactions between molecules containing C=C double bonds over acid catalysts. Another type of reaction that achieves C—C coupling is forming a ketone (plus $CO_2$ and $H_2O$) by reacting two carboxylic acids.

Figure 3:
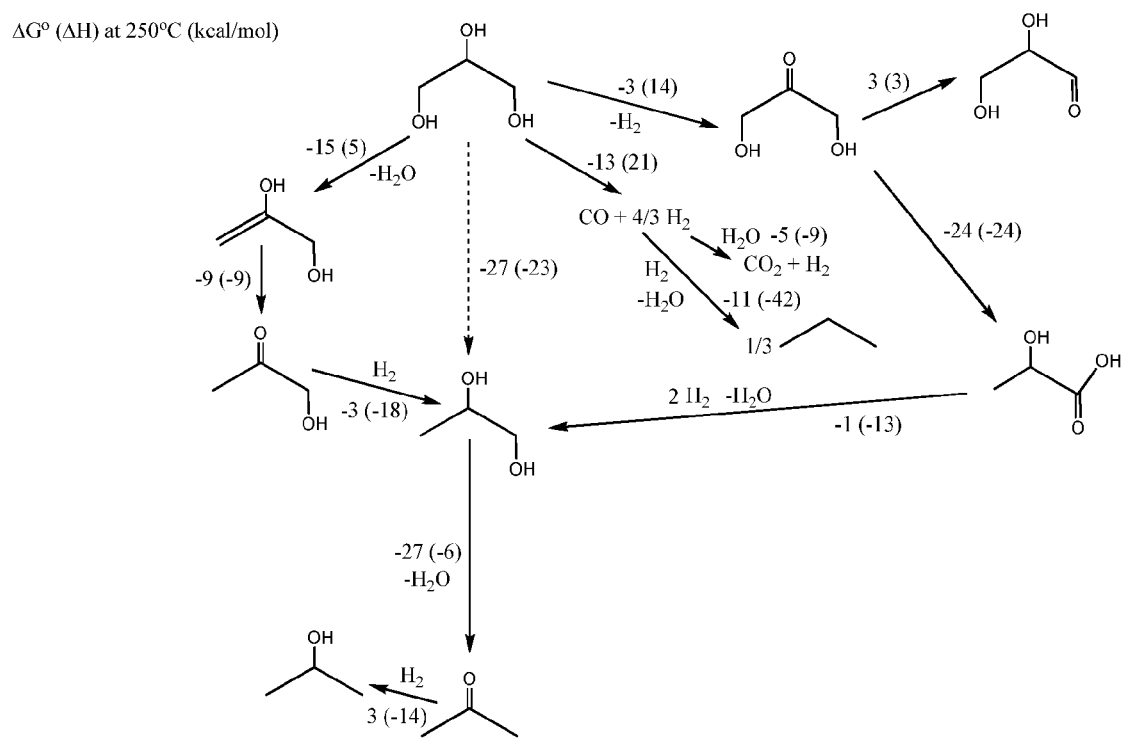
FIG. 3 is a reaction tree depicting changes in standard Gibbs free energy ($\Delta G°$) and enthalpy ($\Delta H$) (both in kcal/mol) at 520 K for reactions involved in converting glycerol to various chemical intermediates. Values not in parentheses correspond to $\Delta G°$, and values within parentheses correspond to $\Delta H$.

FIG. 3 is a reaction tree showing $\Delta G°$ and $\Delta H$ values at 520 K for various reactions involved in converting glycerol to alkanes. It can be seen that dehydrogenation reactions of glycerol to dihydroxyacetone and glyceraldehyde (across the top of FIG. 3) have small values of $\Delta G°$, such that all three species may be present during catalytic processing at 520 K. The subsequent conversion of dihydroxyacetone and glyceraldehyde to lactic acid (lower-right of FIG. 3) is favorable ($\Delta G°=-24$ kcal/mol). As a consequence, the formation of organic acids during the catalytic processing of sugars and polyols represents an important side-reaction in the present invention. The reduction of lactic acid to propanediol is slightly favorable at 520 K ($\Delta G°=-1$ kcal/mol), thus providing a pathway for converting these acidic by-products. The values of $\Delta G°$ for converting polyols to sugars are more negative for $C_5$ and $C_6$ compounds because the sugars of these compounds form $C_5$ and $C_6$ ring structures with hemiacetal groups.

It can be seen in FIG. 3 that the formation of CO and $H_2$ (i.e., synthesis gas) from glycerol at 520 K is thermodynamically favorable ($\Delta G°=-13$ kcal/mol). The formation of synthesis gas is highly endothermic, and the reaction is favorable at 520 K because of an increase in entropy. FIG. 3 also shows that the subsequent conversion of synthesis gas to alkanes (e.g., by Fischer-Tropsch synthesis) is highly exothermic and thus favorable at 520 K ($\Delta G°=-11$ kcal/mol). The combination of the endothermic reaction in which synthesis gas is formed with the exothermic reaction in which synthesis gas is utilized leads to a slightly exothermic reaction for the conversion of glycerol to propane. The conversion of CO with water to produce $CO_2$ and $H_2$ is also favorable at 520 K (i.e., water-gas shift, $\Delta G°=-5$ kcal/mol). Accordingly, the production of synthesis gas from glycerol must be operated at low concentrations of water and/or over catalysts that do not facilitate the water-gas shift reaction ($CO+H_2O \rightarrow CO_2+H_2$).

The hydrogenolysis of a C—O bond in glycerol to form propanediol is thermodynamically favorable at 520 K ($\Delta G°=-27$ kcal/mol). This conversion can be carried out directly (according to the present invention) over supported metal catalysts that are effective for C—O hydrogenolysis reactions. Alternatively, as shown in FIG. 3, this conversion may take place first by dehydration to an enol compound (left-hand side of FIG. 3) ($\Delta G°=-15$ kcal/mol) and to acetol ($\Delta G°=-9$ kcal/mol). In a subsequent step, the C=C or C=O double bonds can then be hydrogenated to produce propanediol ($\Delta G°=-3$ kcal/mol from acetol). This route for converting glycerol to propanediol can be carried out over bi-functional catalysts containing acid or basic sites (to achieve dehydration) and metal sites (to facilitate hydrogenation reactions). The conversion by dehydration of propanediol to acetone is a highly favorable reaction at 520 K ($\Delta G°=-27$ kcal/mol), such that high concentrations of acetone should be expected during this reaction.

Figure 4:
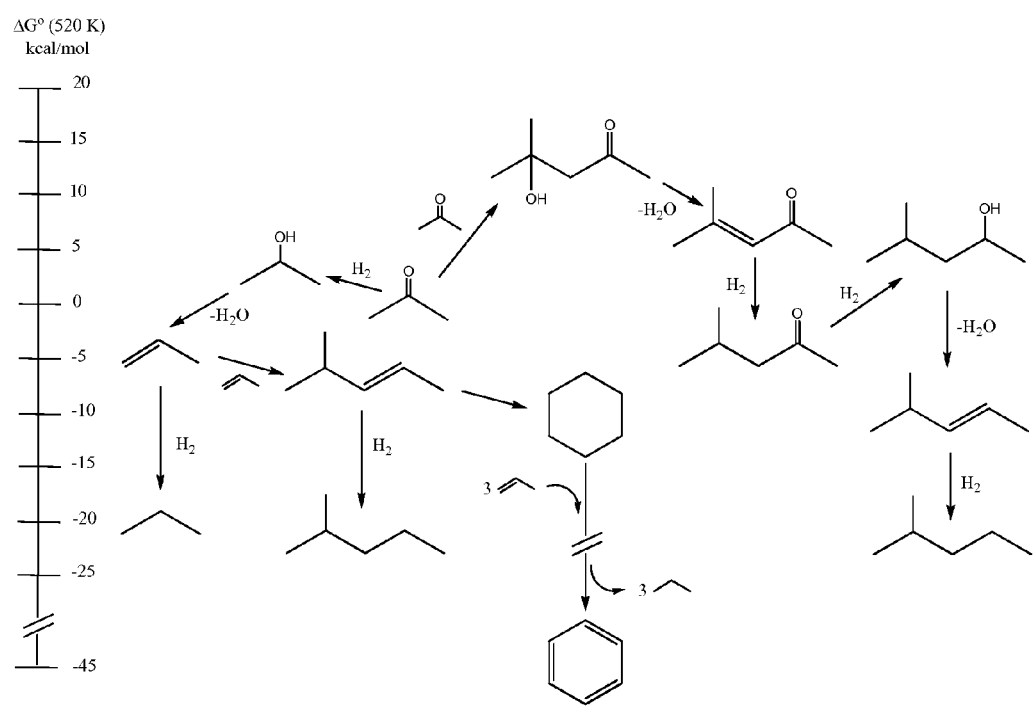
FIG. 4 is a reaction tree depicting changes in standard Gibbs free energy at 520 K (kcal/mol) for reactions involved in converting acetone to liquid fuels.

Thus, one version of the invention produces high concentrations of ketones via catalytic conversion of sugars and polyols. These chemical intermediates can then be used as reactants in C—C coupling reactions, thereby providing a route for the subsequent production of liquid fuels. As shown in FIG. 4, the aldol-condensation of two acetone molecules to form diacetonealcohol is unfavorable at 520 K ($\Delta G°=12$ kcal/mol); however, the dehydration of this intermediate to form mesityloxide is thermodynamically favorable ($\Delta G°=-6$ kcal/mol), such that the formation of mesityloxide from acetone is only slightly unfavorable ($\Delta G°=6$ kcal/mol). Thus, while only low concentrations of mesityloxide are expected under these reaction conditions, the hydrogenation of this intermediate to methylisobutylketone is favorable at 520 K ($\Delta G°=-11$ kcal/mol). In the presence of hydrogen, methylisobutylketone is converted to the corresponding alcohol ($\Delta G°=10$ kcal/mol). While the thermodynamics for this hydrogenation are not favorable at 520 K, the subsequent dehydration of this compound and the hydrogenation of the corresponding olefin to produce 2-methylpentane are highly favorable processes ($\Delta G°=-15$ and $-13$ kcal/mol, respectively). These steps, starting with formation of acetone, followed by aldol-condensation, and completed by various dehydration and hydrogenation processes, define a strategy for producing an alkane having a larger number of carbon atoms than present in the initial polyol reactant (e.g., this version of the invention increases the carbon chain from 3 to 6 atoms when glycerol is used as the feedstock). Aldol condensation reactions are typically carried out over basic catalysts, although acid catalysts may also be used for these reactions. Dehydration reactions take place over acid or basic catalysts, and hydrogenation reactions are typically carried out over metal catalysts.

Another strategy to achieve C—C coupling is to convert acetone by hydrogenation to isopropanol ($\Delta G°=3$ kcal/mol), followed by dehydration over an acid catalyst to propylene ($\Delta G°=-7$ kcal/mol). In this route, the overall conversion of acetone to propylene is thermodynamically favorable. In the presence of excess $H_2$ and an active hydrogenation catalyst, the propylene will be converted to propane ($\Delta G°=-15$ kcal/mol), which generally is undesirable. However, the coupling between two propylene molecules by alkylation over an acid catalyst to form a $C_6$-olefin is favorable at 520 K ($\Delta G°=-2$ kcal/mol), and the equilibrium conversion of propylene to $C_6$-olefin can be increased by operating at lower temperatures (because the reaction is exothermic) or at higher pressures (because the reaction leads to a decrease in the number of molecules). Another possible reaction over an acid catalyst is rearrangement of the $C_6$-olefin to produce cyclohexane, which leads to a decrease in the standard Gibbs free energy by 7 kcal/mol. Importantly, cyclohexane can undergo hydride transfer reactions with propene over an acid catalyst to form benzene and propane, leading to a further decrease in the standard Gibbs free energy by 37 kcal/mol.

IV. Reaction Conditions

Heterogeneous catalysts are used extensively in the conversion of petroleum feedstocks to valuable fuels and chemicals. Studies of catalytic processes for petrochemical applications have thus contributed significantly to the understanding of heterogeneous catalysis. Accordingly, it is instructive to compare the thermodynamic properties of reactions employed in converting oxygenated compounds (e.g., sugars and polyols) versus reactions employed in converting petrochemical feedstocks (e.g., alkanes and olefins). In this respect, a primary difference between these two classes of compounds is that dehydrogenation reactions of oxygenated compounds are thermodynamically more favorable than dehydrogenations of alkanes. For example, the enthalpy changes (at 520 K) for the dehydrogenations of 2-propanol, 1-propanol, and propane to produce acetone, propanal, and propene are 14.1, 16.5, and 30.8 kcal/mol, respectively. These endothermic dehydrogenation reactions are favored at higher temperatures; the temperatures above which the values of $\Delta G°$ become negative are 478, 563, and 913 K, respectively. Thus, at typical reaction temperatures of 520 K and in the presence of hydrogen and metal catalysts to facilitate hydrogenation and dehydrogenation reactions, the concentrations of ketones should be high, the concentrations of aldehydes should be lower, and the concentrations of olefins should be very low.

Another important aspect of the reactivity of oxygenated compounds is that dehydration reactions to form ketones are more favorable compared to dehydration reactions leading to olefins. For example, the enthalpy change (at 520 K) for dehydration of isopropanol to propene is 12.7 kcal/mol. In contrast, the enthalpy change for dehydration of glycerol to acetol is −4.5 kcal/mol. At a typical reaction temperature of 520 K, both of these dehydration reactions are favorable, with values of $\Delta G°$ equal to −6.1 and −23.8 kcal/mol, respectively. It is thus possible to produce high concentrations of ketones from polyols in the presence of hydrogen, because dehydration is favorable while hydrogenation of the ketone to the alcohol is unfavorable.

As described above, the dehydrogenation of alcohols to carbonyl compounds and the dehydration of alcohols to olefins are both thermodynamically favorable at temperatures near 520 K, and hydrogenation reactions of olefins to alkanes are also very favorable. Thus, one strategy used in the present invention to achieve C—C coupling between ketones in the presence of hydrogen at 520 K is to employ a bi-functional catalyst containing basic (or acidic) sites and metal sites, where the basic (or acidic) sites facilitate aldol-condensation and the metal sites facilitate hydrogenation and dehydrogenation reactions. Because the hydrogenation of ketones to alcohols is not favorable at 520 K, the concentration of ketones in the reactor remains high even in the presence of $H_2$, thus allowing bi-molecular aldol-condensation reactions to take place over basic sites. The dehydration of the aldol-adduct (over basic or acid sites) is also favorable at 520 K, such that the thermodynamics for the formation of the dehydrated aldol-adduct from the ketone reactants are only slightly unfavorable. Importantly, however, the hydrogenation (over metal sites) of the dehydrated aldol-adduct involves the hydrogenation of a C═C double bond, which is highly favorable 520 K. Thus, the overall conversion of ketone to the aldol-adduct following dehydration and hydrogenation is highly favorable. For example, the enthalpy change at 520 K when converting two acetone molecules to one MIBK molecule is −24.1 kcal/mol, and the value of $\Delta G°$ is −6.0 kcal/mol. According to the above scenario, the addition of $H_2$ to a feed of ketones at temperatures near 520 K will enhance the extent of C—C coupling between these ketones over a bi-functional catalyst because the equilibrium for converting these ketones to unreactive alcohols is unfavorable at these temperatures. At the same time, the equilibrium for hydrogenation of the aldol-adduct following dehydration is highly favorable. In general, this approach for achieving C—C coupling in the presence of $H_2$ is dependent on the relative rates of metal-catalyzed hydrogenation/dehydrogenation reactions versus non-metal-catalyzed dehydration and aldol-condensation reactions. These relative rates can be controlled by the partial pressure of hydrogen and by the number of metal sites versus the number of non-metal sites on the catalyst.

The dehydration of alcohols to olefins, and the oligomerization of olefins are both favorable processes at temperatures near 520 K. The dehydration process is endothermic ($\Delta H$=12.7 kcal/mol) and is favored at higher temperatures, whereas olefin oligomerization is exothermic ($\Delta H$=−22.1 kcal/mol) and is favored at lower temperatures. The temperature above which the value of $\Delta G°$ for oligomerization becomes positive is equal to 583 K. Therefore, the conversion of alcohols to higher molecular weight olefins must be carried out at temperatures sufficiently high to achieve high rates but sufficiently low to achieve favorable thermodynamics for the formation of oligomers versus olefin monomers. In contrast, converting olefins to aromatics and alkanes is highly favorable at all reaction temperatures, and it is expected that these reactions will dominate at higher temperatures (e.g., 770 K) where olefin oligomerization is thermodynamically unfavorable.

Converting polyols and sugars to organic acids is thermodynamically favorable at typical reaction temperatures. The presence of these acids may inhibit the rates of base-catalyzed reactions, such as aldol-condensation. The strategy for achieving C—C coupling in this instance is to reduce the organic acids to alcohols over metal catalysts (such as Cu or Ru). For example, reducing lactic acid to propanediol is exothermic at 520 K ($\Delta H$=−13.0 kcal/mol), and this reaction is thus favored at lower temperatures. The temperature above which the value of $\Delta G°$ for acid reduction becomes positive is 553 K. In addition to operating at lower temperatures, the equilibrium for reduction of acids to alcohols can be shifted toward alcohols by operating at higher pressures of hydrogen. Another strategy for removing acids is to employ ketonization reactions, for example over ceria at temperatures near 700 K, whereby two acid molecules combine to form a ketone plus $CO_2$ and $H_2O$.

V. Converting Polyols to Alcohols and Ketones:

The thermodynamic data summarized in FIGS. 3 and 4 indicates that an effective strategy for converting carbohydrates to fuels is first to produce ketones and alcohols (as given in FIG. 3), and then to achieve C—C coupling over acid or base catalysts to produce liquid fuels (as given in FIG. 4). An important benefit of this two-stage approach is that the ketones and alcohols produced during the first stage are themselves valuable commodity compounds for the chemical industry. According to the present invention, it has been discovered that the conversion of sugars and polyols to alcohols and ketones can be carried out with high yields over Pt—Re/C catalysts at temperatures near 500 K, as disclosed and claimed herein.

The conversion of polyols over Pt—Re/C proceeds via reaction pathways that involve C—C and C—O bond scission. High rates of C—C cleavage lead to the formation of CO and $CO_2$, whereas, high rates of C—O cleavage produce alkanes. Decreasing this rate of C—O cleavage shifts production from alkanes to oxygenated hydrocarbon compounds (e.g., alcohols, ketones, and polyols). The catalytic conversion of an aqueous glycerol feed over a Pt—Re/C catalyst at temperatures from 480-520 K leads to the formation of gaseous products (CO, $CO_2$, and $C_1$-$C_3$ alkanes) in addition to light alcohols, acetone, and diols in the aqueous liquid effluent. Gas mixtures of CO, $CO_2$, and light alkanes are also produced from the catalytic processing of aqueous sorbitol feeds at these conditions. However, the liquid effluent separates spontaneously at room temperature into an organic phase containing alcohols, ketones, acids, and alkanes with 4, 5, or 6 carbon atoms, as well as tetrahydrofuran and tetrahydropyran compounds, and an aqueous phase containing more highly oxygenated organic compounds (e.g., diols, isosorbide). To determine the effects of process conditions and feed molecule on the rates of C—C and C—O bond cleavage over Pt—Re/C, reaction kinetics studies were conducted for the conversion of concentrated aqueous solutions of glycerol (80 wt % in water) and sorbitol (60 wt % in water) over a 10 wt % Pt—Re/C catalyst with a Pt:Re atomic ratio of 1:1 at various temperatures and pressures. An investigation was also carried out regarding the changes in selectivities toward $CO_x$ species, alkanes, highly oxygenated-water soluble compounds, and high molecular-weight mono-oxygenated hydrocarbons (e.g., $C_4$-$C_6$ alcohols and ketones).

Figure 5:
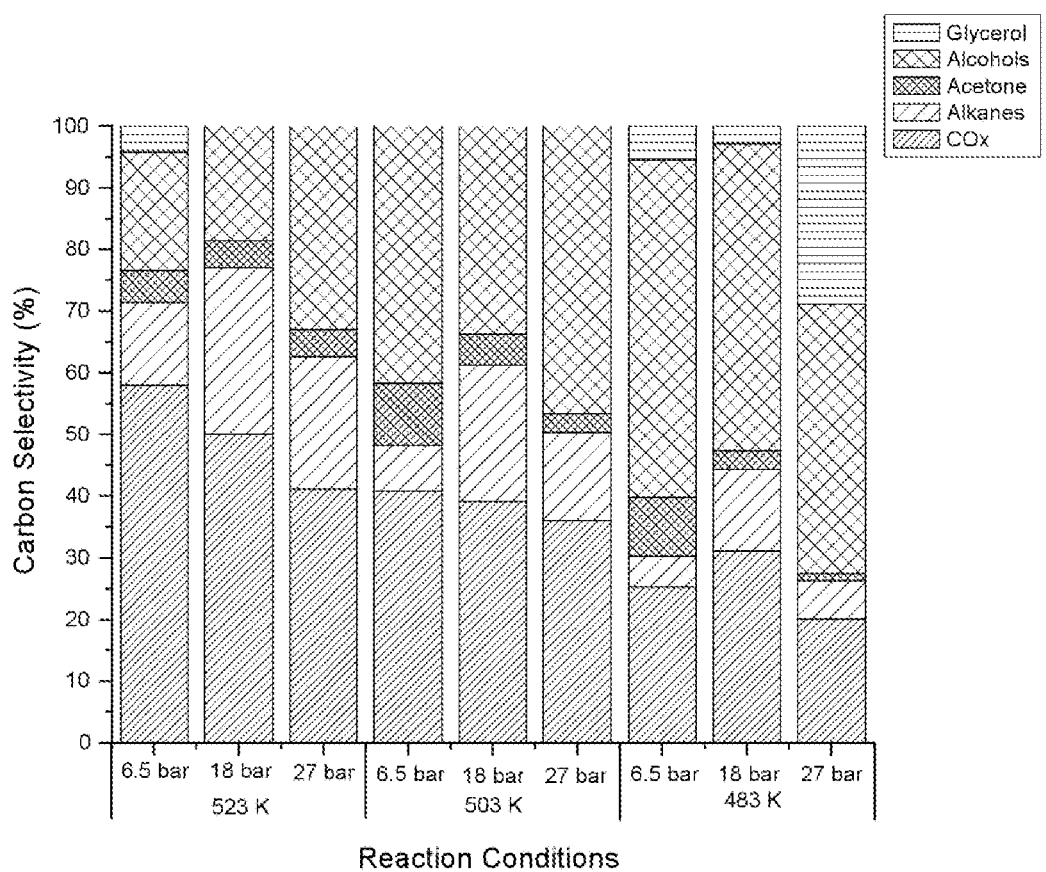
FIG. 5 is a histogram depicting carbon selectivities for converting glycerol over 10 wt % Pt—Re/C at temperatures between 483-523 K and pressures of 6.5 bar, 18 bar, and 27 bar according to the present invention. Reactions were carried out using 0.04 mL min$^{-1}$ of an 80 wt % glycerol feed and 3.0 g catalyst (WHSV=0.75 h$^{-1}$).

FIG. 5 is a histogram showing the effect of varying pressure on carbon selectivities for the conversion of an 80 wt % glycerol solution at temperatures between 483 K and 523 K. At constant temperature, an increase in pressure from 6.5 bar to 18 bar results in an increase in alkane production at the expense of $CO_x$ species, alcohols/diols, and acetone. However, further increasing the pressure to 27 bar causes the production of oxygenated hydrocarbons in the aqueous phase to increase while gaseous species production (alkanes and $CO_x$) decreases. These results indicate a shift in selectivity from C—C bond breaking at low pressures to C—O bond breaking at higher pressures. As pressure increases, the rate of C—O bond cleavage slows, and the production of more oxygenated species (alcohols) favors the production of alkanes. The $CO_x$/(Alcohol+Ketone) and $CO_R$/Alkane ratios listed in Table 1 (below) decrease with increasing pressure, further showing the shift in selectivity from $CO_x$ species from C—C cleavage to oxygenated hydrocarbons and alkanes from C—O bond cleavage as pressure increases. The decrease in $CO/CO_2$ ratio indicates an increase in the rate of the water-gas shift reaction at higher partial pressures of water. Decreasing temperature at constant pressure has a similar effect as increasing pressure. The production of CO and $CO_2$ decreases with an increase in the production of alkanes and oxygenates in the aqueous phase, thus indicating a decrease in C—C scission and an increase in C—O scission. As mentioned previously, high rates of C—C bond cleavage lead to the production of gaseous $CO/CO_2$ and high rates of C—O bond cleavage produce alkanes. As temperature decreases, the ratio of $CO_x$/(Alcohol+Ketone) decreases, however, the $CO_R$/Alkane ratio remains similar. This result shows that decreasing temperature slows both C—C and C—O bond cleavage leading to the production of alcohols, diols, and acetone. This result is similar to the effect of increasing pressure. The appearance of unreacted glycerol in the liquid effluent at low temperature (483 K) and high pressure (27 bar) further indicates the decrease in both C—C and C—O bond scission. Each set of conditions was stable for at least 24 hours time-on-stream, and the carbon balance for each condition closed to within 10%.

TABLE 1

Molar carbon ratios for the conversion of glycerol over 10 wt % Pt—Re/C at pressures of 6.5 bar, 18 bar, and 27 bar and temperatures of A.) 523 K, B.) 503 K, and C.) 483 K. Reactions carried out using 0.04 mL $min^{-1}$ of an 80 wt % glycerol feed and 3.0 g catalyst (WHSV = 0.75 $h^{-1}$).

|  | 6.5 bar | 18 bar | 27 bar |
| --- | --- | --- | --- |
| A.) 523 K |  |  |  |
| $CO_x$/Alkanes | 4.36 | 1.86 | 1.91 |
| $CO_x$/(Alcohol + Ketone) | 2.39 | 2.18 | 1.10 |
| $CO/CO_2 \times 10$ | 8.32 | 0.75 | 0.32 |
| B.) 503 K |  |  |  |
| $CO_x$/Alkanes | 5.52 | 1.77 | 2.53 |
| $CO_x$/(Alcohol + Ketone) | 0.79 | 1.01 | 0.72 |
| $CO/CO_2 \times 10$ | 5.73 | 0.58 | 0.28 |
| C.) 483 K |  |  |  |
| $CO_x$/Alkanes | 5.06 | 2.35 | 3.28 |
| $CO_x$/(Alcohol + Ketone) | 0.39 | 0.59 | 0.45 |
| $CO/CO_2 \times 10$ | 1.79 | 0.16 | 0.08 |

As mentioned previously, in addition to $CO/CO_2$/light alkane gas mixtures and light oxygenated hydrocarbon aqueous-phase products, the conversion of sorbitol over Pt—Re/C also produces a hydrophobic product phase containing ketones, acids, and alkanes with 4, 5, or 6 carbon atoms, as well as tetrahydrofuran and tetrahydropyran compounds. FIGS. 6A and 6B and Table 2 show the effects of temperature, pressure, and space velocity on the selectivities and carbon distributions, respectively, for the conversion of a 60 wt % sorbitol solution over Pt—Re/C. Increasing pressure from 18 bar to 27 bar at 483 K results in a shift of the effluent carbon from aqueous phase species to organic phase species (Table 2a). Increasing pressure at 503 K results in a shift from aqueous phase species to gaseous species (Table 2b), whereas pressure has a negligible effect on the carbon distribution at 523 K (Table 2c). The carbon exiting the reactor from sorbitol conversion consists primarily of alkanes and high molecular weight oxygenated compounds ($C_4$-$C_6$ alcohols, ketones, and acids), and the production of $CO_x$ species remains similar (20-30% of total carbon in products) for all conditions (FIG. 6A). However, the production of alkanes increases at the expense of high molecular-weight oxygenated species as pressure increases at constant temperature. Increasing temperature at constant pressure has a similar effect in that alkanes increase while high molecular weight oxygenates decrease. In addition, the amount of water-soluble, oxygenated hydrocarbons decreases with increasing pressures and/or temperatures. An increase in the space velocity from 0.60 $h^{-1}$ to 1.2 $h^{-1}$ at constant temperature and pressure causes increased production of organic phase species at the expense of gaseous products (FIG. 6B and Table 2d). Furthermore, the amount of ketones, alcohols, and acids increases while the concentration of alkanes decreases. However, a further increase of space velocity to 2.4 $h^{-1}$ shifts the carbon distribution in the products toward aqueous phase oxygenates. In summary, low temperature, low pressure, and high space velocity favor the formation of high molecular weight organic oxygenates ($C_4$-$C_6$ alcohols and ketones) at the expense of $CO_x$ species. The ketone/alcohol ratios decrease with decreasing temperature and increasing pressure, which is in agreement with the thermodynamic analyses of the hydrogenation of a ketone to an alcohol. The $CO/CO_2$ ratios for each condition were on the order of $10^{-2}$. Of the $CO_2$ produced, 70-80% was associated with the production of alkanes from sorbitol as dictated by the following stoichiometric equation for the conversion of a polyol, such as sorbitol, to an alkane:

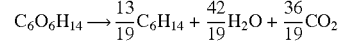

This stoichiometric $CO_2$ corresponds to between 15% and 20% of the total carbon in the products. All reaction conditions were stable for 24 hours time-on-stream, and the carbon balances closed to within 10%.

TABLE 2

Molar carbon distributions for the conversion of sorbitol over 10 wt % Pt—Re/C using 0.04 mL $min^{-1}$ of a 60 wt % sorbitol feed and 3.0 g catalyst (WHSV = 0.60 $h^{-1}$) at 18 bar and 27 bar and temperatures of A.) 523 K, B.) 503 K, and C.) 483 K and at 27 bar and 503 K with flow rates of 60 wt % sorbitol between 0.04-0.16 mL $min^{-1}$ (3.0 g catalyst; WHSV = 0.60-2.4 $h^{-1}$).

|  | 18 bar | 27 bar |
| --- | --- | --- |
| A.) 523 K |  |  |
| % Gas | 53% | 54% |
| % Organic | 43% | 44% |

TABLE 2-continued

Molar carbon distributions for the conversion of sorbitol over 10 wt % Pt—Re/C using 0.04 mL min$^{-1}$ of a 60 wt % sorbitol feed and 3.0 g catalyst (WHSV = 0.60 h$^{-1}$) at 18 bar and 27 bar and temperatures of A.) 523 K, B.) 503 K, and C.) 483 K and at 27 bar and 503 K with flow rates of 60 wt % sorbitol between 0.04-0.16 mL min$^{-1}$ (3.0 g catalyst; WHSV = 0.60-2.4 h$^{-1}$).

|  |  |  |  |
|---|---|---|---|
| % Aqueous | 4% | 2% | |
| B.) 503 K | | | |
| % Gas | 36% | 49% | |
| % Organic | 52% | 48% | |
| % Aqueous | 12% | 4% | |
| C.) 483 K | | | |
| % Gas | 26% | 30% | |
| % Organic | 46% | 57% | |
| % Aqueous | 29% | 13% | |
| D.) 503 K, 27 bar | 0.6 h$^{-1}$ | 1.2 h$^{-1}$ | 2.4 h$^{-1}$ |
| % Gas | 49% | 33% | 28% |
| % Organic | 48% | 60% | 49% |
| % Aqueous | 4% | 7% | 24% |

Comparing the carbon selectivities for conversion of glycerol and sorbitol over Pt—Re/C shows that under the conditions of these studies, glycerol produces more CO$_R$ and light alcohol species, whereas sorbitol gives more alkanes and high molecular-weight oxygenates. The temperature and pressure trends are similar for each molecule with respect to changes in the relative rates of C—C and C—O bond cleavage. The desirable catalytic properties of Pt-based catalysts for reforming oxygenated hydrocarbons to produce CO/CO$_2$/H$_2$ gas mixtures are related to the high rate and selectivity of Pt-containing surface sites for cleavage of C—C versus C—O bonds. In particular, results from density functional theory (DFT) calculations suggest that cleavage of C—C bonds on Pt for an oxygenated hydrocarbon such as ethanol takes place through transition states that have lower energy and that are more dehydrogenated compared to transition states for cleavage of C—O bonds. See Alcala et al., "DFT studies for cleavage of C—C and C—O bonds in surface species derived from ethanol on Pt(111)," *J. Catal.* 218, 178-190 (2003). Because these transition states are multiply bonded to the surface, the rate of C—C bond cleavage is expected to be highly dependent on the coverage provided by abundant adsorbed species which block surface sites, such as adsorbed CO and various other reaction intermediates. While not being bound to any particular mechanism, the unique catalytic properties of Pt—Re-based catalysts are likely related to the promotion by Re of the rate of formation of CO/CO$_2$/H$_2$ gas mixtures on Pt-containing sites, combined with the ability of Re-containing surface sites to facilitate the water-gas shift reaction, as well as the hydrogenolysis of C—O bonds in oxygenated hydrocarbons. See Sato et al., "Mechanistic study of water-gas-shift reaction over TiO$_2$ supported Pt—Re and Pd—Re catalysts," *Appl. Catal. A-Gen.* 296, 80-89 (2005) and Pallassana & Neurock, "Reaction paths in the hydrogenolysis of acetic acid to ethanol over Pd(111), Re(0001), and PdRe alloys," *J. Catal.* 209, 289-305 (2002). Because the binding energies of oxygen atoms and hydroxyl groups are much stronger on Re than on Pt (Zhang et al., "Mixed-metal Pt monolayer electrocatalysts for enhanced oxygen reduction kinetics," *J. Am. Chem. Soc.* 127, 12480-12481 (2005)), these effects of Re on the catalytic properties of Pt—Re-based catalysts may be caused by the presence of oxygen species, especially hydroxyl groups, associated with Re atoms on the surface of Pt—Re alloy particles. A schematic rendering of the effect is presented in FIG. 7.

Figure 7:
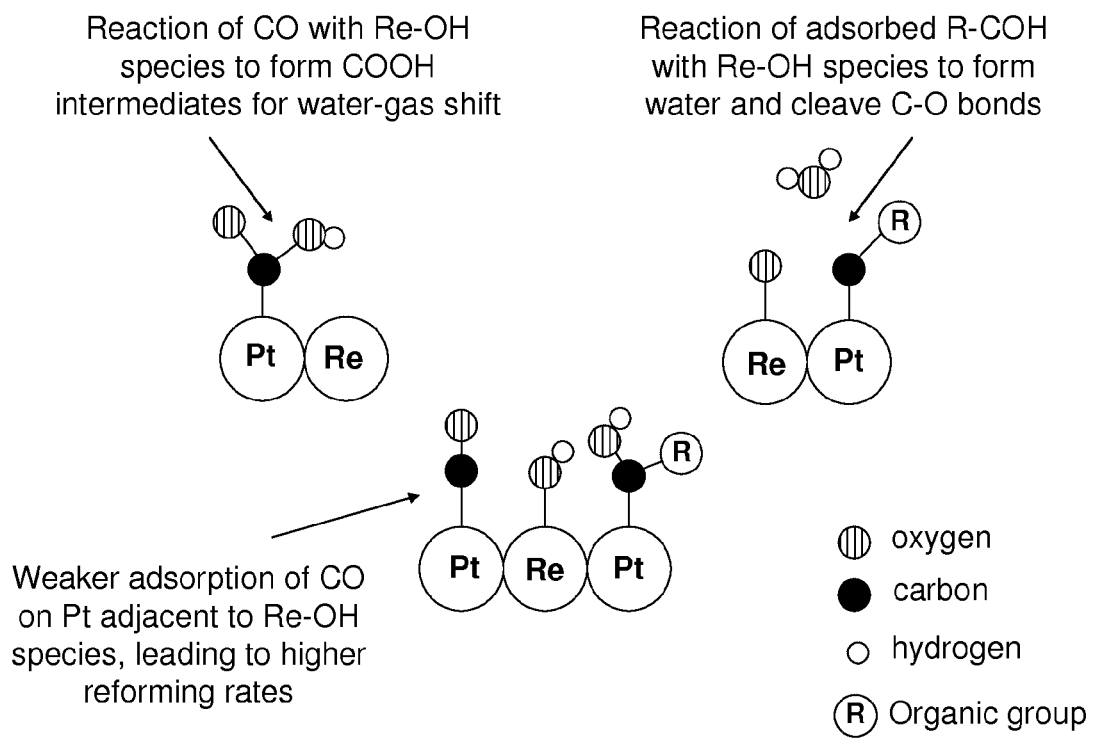
FIG. 7 is a schematic representation of effects of Re—OH species on the catalytic properties of Pt—Re catalysts for reforming of oxygenated hydrocarbons according to one version of the present inventions. The depiction is schematic only; the invention described and claimed herein is not limited to any specific mechanism of action.

Density Functional Theory results show that the central Re surface atom in FIG. 7 is predicted to weaken the strength of CO adsorption on the neighboring surface Pt atom, thereby lowering the CO coverage on Pt-sites during reforming reactions at low temperatures (e.g., 500 K). This leads to higher rates of formation of CO/CO$_2$/H$_2$ gas mixtures from oxygenated hydrocarbons. Greeley & Mavrikakis, "Near-surface alloys for hydrogen fuel cell applications," *Catal. Today* 111, 52-58 (2005). Furthermore, the hydroxyl groups on Re may react with CO adsorbed on neighboring Pt sites (the left portion of FIG. 7), leading to the formation of —COOH species, which are reactive intermediates for the water-gas shift reaction on Pt. Mhadeshwar & Vlachos, "Microkinetic modeling for water-promoted CO oxidation, water-gas shift, and preferential oxidation of CO on Pt," *J. Phys. Chem. B* 108, 15246-15258 (2004). In addition, these hydroxyl groups on Re may serve as a hydrogen transfer agents for reaction with hydroxyl groups in oxygenated hydrocarbon species associated with neighboring Pt sites (the right portion of FIG. 7), leading to cleavage of the C—OH bond by dehydration of the oxygenated hydrocarbon.

The schematic in FIG. 7 for Pt—Re-based catalysts is consistent with the effects measured on the catalytic properties of increasing the system pressure for glycerol reforming. From the results discussed above, increasing the system pressure decreases the CO:CO$_2$ ratio and shifts the product selectivity for glycerol reforming toward alkanes and oxygenated hydrocarbons at the expense of CO/CO$_2$. In particular, higher system pressures and lower system temperatures lead to higher partial pressures and higher surface coverages by the CO and hydrogen products from reforming. Because the transition states for reforming reactions are multiply bonded to the surface and thus require multiple surface Pt atoms, the higher coverages by adsorbed products inhibit the rate of C—C bond cleavage. In addition, the higher pressure of hydrogen may also inhibit the rate of C—C bond cleavage during glycerol reforming over Pt by shifting the equilibrium away from the hydrogen-deficient adsorbed intermediates that lead to cleavage of C—C bonds.

In contrast, the rate of water-gas shift over Pt—Re would be less sensitive to system pressure because Re—OH surface sites would not be poisoned by higher pressures of CO as evidenced by the decrease in the CO:CO$_2$ ratio at higher system pressures. This effect is analogous to the behavior of the water-gas shift reaction on supported metal catalysts containing reducible oxide supports. In the water-gas shift reaction, CO adsorption on Pt does not inhibit the rate of water dissociation on the reducible support, and the rate of the overall reaction is thus uninhibited by CO at elevated pressures. Phatak et al., "Kinetics of the water-gas shift reaction on Pt catalysts supported on alumina and ceria," *Catal. Today* 123, 224-234 (2007). This same behavior also explains why the selectivity toward alkanes and oxygenated hydrocarbons for glycerol reforming over Pt—Re increases at higher system pressures. Specifically, the rate of C—C bond cleavage and thus formation of CO/CO$_2$/H$_2$ from glycerol is slower at higher pressures of CO and H$_2$. In contrast, the formation of alkanes and oxygenated hydrocarbons from glycerol involves the participation of hydroxyl groups associated with Re, which is not highly dependent on system pressure.

Furthermore, FIG. 7 predicts an important effect when changing the reactant from glycerol to sorbitol. The rate of glycerol reforming to produce CO/CO$_2$/H$_2$ over Pt—Re catalysts is low-order with respect to the glycerol pressure, suggesting that the surface Pt sites are highly covered by oxygenated hydrocarbon intermediates. Accordingly, the rate of sorbitol reforming to produce $CO/CO_2/H_2$ is expected to be slower than the rate of glycerol reforming under the same reaction conditions, because the higher number of hydroxyl groups in sorbitol is expected to increase the heat of adsorption of sorbitol-derived species on Pt compared to glycerol-derived species, leading to more extensive blocking of Pt sites for reforming reactions. The results from the studies of sorbitol reforming according to the present invention are in agreement with this prediction. Specifically, the selectivity toward $CO_x$ species is lower when sorbitol is the feed molecule compared to glycerol as the feed molecule. Additionally, the normalized rate of $H_2/CO/CO_2$ production over Pt—Re/C at 503 K and 18 bar using glycerol as the feed molecule is 1.6 $min^{-1}$, whereas this value is 0.8 $min^{-1}$ using sorbitol as the feed molecule.

According to the above observations, the conversion of sorbitol over Pt—Re-based catalysts will yield high selectivities for C—O bond cleavage, leading to the formation of long-chain alcohols and ketones (such as hexanol and hexanone). Glycerol conversion will lead to high selectivities for the formation of synthesis gas via C—C bond cleavage. Indeed, the results from reaction kinetics studies of glycerol and sorbitol conversion over Pt—Re/C at various temperatures and pressures agree with this prediction. (See the Examples.) It should be noted that cleavage of all C—O bonds in sorbitol leads to the formation of hexane. However, because the binding strength to the surface is expected to decrease as more oxygen atoms are removed from sorbitol, it is possible that long-chain alcohols and ketones would desorb from the surface and be replaced by more strongly adsorbed reactant molecules. Thus, in the present invention sorbitol is selectively converted to long-chain alcohols and ketones while minimizing the formation of hexane. Indeed, the results from reaction kinetics studies presented in the Examples below show that converting an aqueous solution of sorbitol over Pt—Re/C at temperatures near 503 K leads to the formation of two liquid phases that spontaneously separate from each other at the reactor effluent: the aqueous effluent phase contains about 10% of the effluent carbon (as light alcohols and acetone), and the organic effluent phase contains about 55% of the effluent carbon (primarily as hexane, sec-pentanols, sec-hexanols, pentanones, and hexanones). The gas phase effluent contains 35% of the carbon, comprised primarily by $CO_2$ and light alkanes. Impressively, more than 50% of the effluent carbon from sorbitol conversion comprises of alkanes and hydrophobic, long-chain alcohols and ketones, along with about 20% of the effluent carbon being stoichiometric $CO_2$ that was required to produce alkanes from sorbitol.

Figure 8:
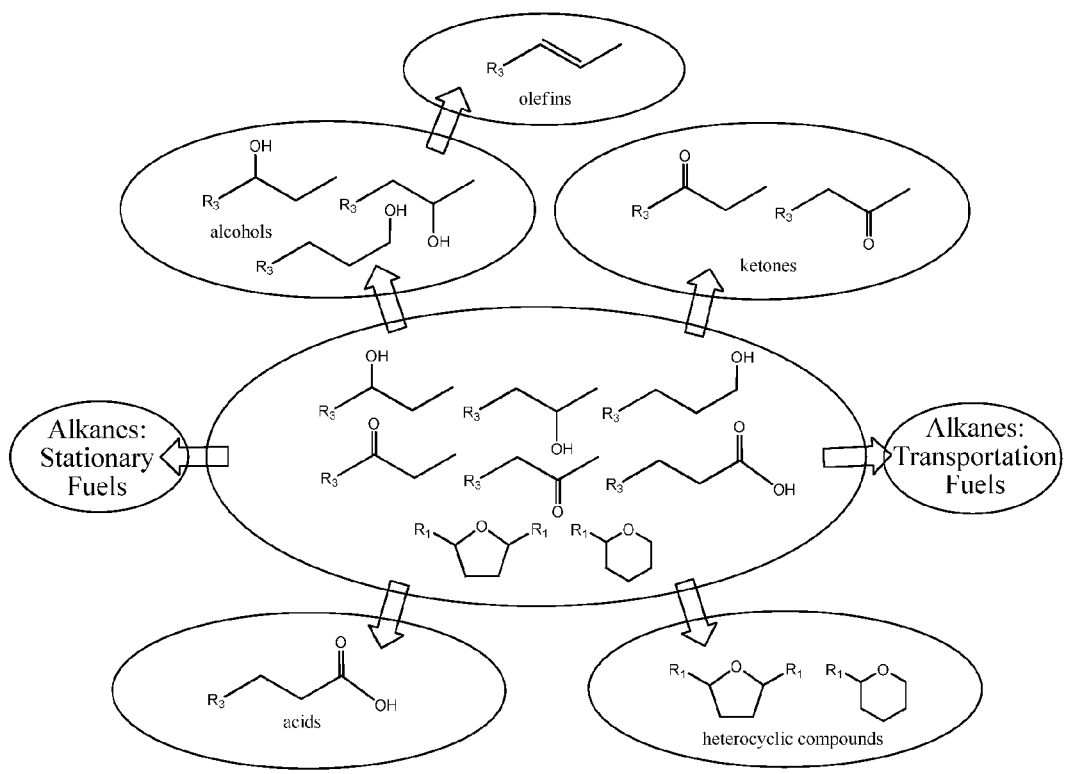
FIG. 8 is a schematic diagram depicting mono-functional organic compounds derived from sorbitol as a platform for producing fuels and chemicals according to the present invention. $R_3$ represents alkyl, preferably lower alkyl (and most preferably $CH_3$, $CH_3CH_2$ or $CH_3CH_2CH_2$ groups), and $R_1$ represents H, alkyl, or lower alkyl (preferably $CH_3$).

VI. Mono-Oxygenated Organic Compounds as a Platform for Fuels and Chemicals:

FIG. 8 summarizes the classes of mono-oxygenated organic compounds produced according to the present invention from the catalytic processing of sorbitol over a Pt—Re/C catalyst at temperatures near 500 K. The wide variety of compounds and the diverse uses of these compounds show that the organic liquid stream produced from sorbitol over Pt—Re/C according to the present invention serves as a valuable intermediate platform for converting renewable biomass resources to fuels and chemicals. This platform can be used to produce alkane fuels for high-volume stationary or transportation applications by controlling the extent of C—C bond coupling during the removal of oxygen atoms to produce alkanes. Alternatively, the inventive method can be tuned to favor the production of alcohols versus the production of ketones, depending on the needs of the user. The production of alcohols can be followed by the formation of olefins for the polymer industry. Furthermore, the organic acids present in this liquid can be converted to alcohols, or they can be extracted for chemical applications. Finally, the heterocyclic compounds present in this liquid can be extracted for use as solvents or as blending agents in transportation fuels.

The predominant intermediates that are produced by the catalytic processing of sorbitol (60 wt % in water) over a Pt—Re/C catalyst at temperatures near 500 K are alcohols, ketones, acids, and alkanes containing 4, 5, or 6 carbon atoms, as well as tetrahydrofuran and tetrahydropyran compounds. Aldehydes are not produced in significant amounts because these compounds are converted to primary alcohols in the presence of $H_2$ that is produced co-currently by aqueous-phase reforming. The liquid effluent from the Pt—Re/C catalyst separates spontaneously at room temperature into an organic phase containing the aforementioned compounds and an aqueous phase containing more highly oxygenated organic compounds (e.g., diols, isosorbide) in the water that is fed to the reactor as well as water that is produced during reaction. The liquid organic effluent phase serves as a precursor for the production of chemicals or liquid fuels. For example, the organic phase can be processed in the presence of $H_2$ over a Ru/C catalyst at temperatures near 400 K to reduce the ketones and acids to alcohols, thereby producing a liquid organic stream consisting primarily of mono-oxygenated $C_4$-$C_6$ compounds. The effluent from this process serves as a source of compounds for various chemical applications (e.g., solvents). In addition, the alcohols can undergo dehydration over an acid catalyst at temperatures near 520 K to produce olefins for polymer applications. The mono-oxygenated $C_4$-$C_6$ compounds are also useful as blending agents in transportation fuels.

The alcohols in the liquid organic stream produced over Ru/C at 400 K can be converted to ketones by catalytic processing over a Cu catalyst at temperatures near 570 K, for which the equilibrium constant for dehydrogenation of a secondary alcohol to a ketone is favorable ($K_{eq}$~10). This production of ketones can be accomplished by passing the effluent from the Pt—Re/C catalyst directly over the Cu catalyst at 570 K, thereby eliminating the reduction step using the Ru catalyst because Cu-based catalysts are effective for reduction of organic acids to alcohols at elevated temperatures. The organic liquid effluent from the Cu catalyst would then serve as a source of ketones for various chemical applications (e.g., paints, solvents).

Importantly, the $C_4$-$C_6$ ketones in this organic liquid can undergo C—C coupling by aldol-condensation over basic catalysts to produce $C_8$-$C_{12}$ compounds that can undergo subsequent hydrodeoxygenation processing (e.g., over $Pt/Nb_2O_5$ at 550 K) to produce $C_8$-$C_{12}$ alkanes. The aldol-condensation step can be carried out at 570 K in the presence of $H_2$ over a bi-functional $Cu/MgAl_2O_4$ catalyst, where the $MgAl_2O_4$ component provides the required basic sites for aldol-condensation, and Cu is present to provide sites for hydrogenation of C=C double bonds in dehydrated aldol-adducts, thereby improving the overall thermodynamics for the process. At these reaction conditions, 2-ketones can undergo self-aldol condensation or crossed-aldol condensation with 3-ketones, whereas 3-ketones do not undergo self-aldol condensation (because the C=O group is not adjacent to a primary carbon atom). In addition, the primary alcohols present in the liquid organic phase can undergo crossed-aldol condensation with ketones (probably taking place via the intermediate formation of aldehydes).

Another route for producing liquid fuels according to the present invention is simply to use the liquid organic effluent stream from the Pt—Re/C catalyst as the feed to an acid catalyst, such as ZSM-5 at elevated temperatures (e.g., 670 K). Oxygenated organic compounds present in the feed, such as alcohols, ketones, and acids, can be converted over an acid catalyst (ZSM-5) to gasoline components, such as aromatics, olefins, and $C_{5+}$ paraffins. This conversion takes place through a complex series of reactions, including dehydration, aldol condensation, alkylation, ketonization, and aromatization. A significant advantage of this approach for producing liquid fuel is that the process consists of two catalytic reactors, in which the effluent from the first reactor is fed without clean-up to the second reactor, leading to savings in capital costs. This approach, however, leads to a liquid fuel having a wide variety of chemical components. In contrast, the approach for producing liquid fuels based on the intermediate formation of ketones, followed by aldol-condensation, has the potential for producing a more controlled distribution of fuel components, but at a higher capital cost.

VII. Examples of Converting Sorbitol to Liquid Fuels:

The following Examples are included solely to provide a more complete description of the invention disclosed and claimed herein. The Examples do not limit the scope of the invention in any fashion.

In this Example, $C_4$-$C_6$ ketones and secondary alcohols in the organic liquid derived from converting sorbitol over Pt—Re/C underwent C—C coupling by aldol condensation over basic catalysts to produce $C_8$-$C_{12}$ compounds. These compounds were then subjected to hydrodeoxygenation (over Pt/$Nb_2O_5$ at 548 K) to yield $C_8$-$C_{12}$ alkanes. The aldol condensation step was carried out at 573 K in the presence of $H_2$ over a bi-functional $CuMg_{10}Al_7O_x$ catalyst, where the $Mg_{10}Al_7O_x$ component provides sites for aldol condensation, and the Cu provides sites for hydrogenation of C=C double bonds in dehydrated aldol-adducts. This improves the overall thermodynamics for the process; dehydrogenation of secondary alcohols to ketones is a process that is thermodynamically favored at these reaction conditions.

Small amounts of organic acids and esters were present in the organic liquid fraction derived from converting sorbitol. These organic acids and esters were removed prior to aldol condensation because these compounds cause deactivation of the catalyst, probably by adsorbing strongly on basic sites. To this end, organic liquid from sorbitol conversion over Pt—Re/C was refluxed with a 20 wt % NaOH solution at 343 K and atmospheric pressure to hydrolyze esters and neutralize organic acids. Subsequently, this treated organic liquid was passed over a $CuMg_{10}Al_7O_x$ catalyst at 573 K and 5 bar pressure with 20 mL $min^{-1}$ $H_2$ co-feed (weight hourly space velocity of feed equal to 0.4 $h^{-1}$). FIG. 9A shows the resulting product distribution.

At these reaction conditions, 2-ketones undergo self-aldol condensation or crossed-aldol condensation with 3-ketones, whereas self-aldol condensation of 3-ketones is less likely due to steric and electronic effects. The primary alcohols present in the liquid organic phase undergo crossed-aldol condensation with ketones (taking place via the intermediate formation of aldehydes). Light species containing between 4 and 6 carbon atoms and 1 or no oxygen atoms ($C_4$-$C_6$) comprise 55% of the carbon in the products, caused primarily by the low reactivity for condensation of 3-ketones. These light species contain $C_4$ alcohols (3% of total carbon) and heterocyclic hydrocarbon compounds (substituted tetrahydrofurans and tetrahydropyrans; 9% of total carbon) which will form $C_4$-$C_6$ alkanes upon hydrodeoxygenation. $C_5$-$C_6$ ketones and secondary-alcohols contribute 32% of the carbon in the products while hexane and pentane contribute 10% of the carbon. The remaining carbon (45%) is associated with condensation products containing between 8 and 12 carbon atoms and 1 or no oxygen atoms ($C_8$-$C_{12}$). The condensation products can be converted by hydrodeoxygenation to the corresponding alkane products, leading to a distribution similar to that shown in FIG. 9A. Alternatively, the $C_8$-$C_{12}$ fraction can be separated from the $C_4$-$C_6$ fraction and converted to heavy alkane products, while the $C_4$-$C_6$ fraction (comprised primarily of 3-hexanone, 3-pentanone, tetrahydrofurans, and tetrahydropyrans) can be used as fuel additives, solvents or chemical intermediates.

Liquid fuel components can also be produced by reacting oxygenated hydrocarbons over H-ZSM-5 to produced aromatics, olefins and paraffins. In this Example, the organic liquid produced from sorbitol over Pt—Re/C was converted to liquid fuel components by first hydrogenating the ketones to alcohols (at 433 K and 55 bar $H_2$ pressure over 5 wt % Ru/C), followed by dehydration/alkylation/aromatization at 673 K and atmospheric pressure over H-ZSM-5. As shown in FIG. 9B, which is a pie chart depicting the product mix, 24.6% and 29.4% of the carbon in the sorbitol-derived organic phase is converted to paraffins and olefins containing 3 and 4 carbon atoms, respectively, while 38.2% of the carbon is converted to aromatic species. Of this aromatic fraction, 12.4%, (4.7% of total) and 37.3% (14.2% of the total) is converted to benzene and toluene, respectively, while 28.7% (11% of the total) is converted to a C-2 benzene (a benzene with two additional carbon atoms such as xylenes, or ethyl benzene). The remaining 21.6% of the aromatic fraction (8.2% of the total) is split between $C_3$-$C_6$ substituted benzene.

What is claimed is:

1. A method for preparing liquid fuel and chemical intermediates from biomass-derived oxygenated hydrocarbons, the method comprising:

reacting in a single reactor an aqueous solution of a biomass-derived, water-soluble oxygenated hydrocarbon reactant, in the presence of a catalyst comprising a metal selected from the group consisting of Cr, Mn, Fe, Co, Ni, Cu, Mo, Tc, Ru, Rh, Pd, Ag, W, Re, Os, Ir, Pt, and Au, at a temperature, and a pressure, and for a time sufficient to yield a self-separating, three-phase product stream comprising:

a vapor phase;

an organic phase comprising linear or cyclic mono-oxygenated hydrocarbons;

and an aqueous phase.

2. The method of claim 1, wherein the catalyst comprises platinum.

3. The method of claim 1, wherein the catalyst comprises platinum and rhenium.

4. The method of any one of claim 1, 2, or 3, wherein the catalyst is disposed on a support.

5. The method of claim 4, wherein the support is selected from the group consisting of silica, alumina, zirconia, titania, ceria, vanadia, carbon, heteropolyacids, silica-alumina, silica nitride, boron nitride, and mixtures thereof.

6. The method of claim 4, wherein the support is selected from the group consisting of zeolites, nanoporous carbon, nanotubes, and fullerenes.

7. The method of claim 1, wherein the catalyst comprises platinum, rhenium, or a combination of platinum and rhenium, disposed on a support selected from the group consisting of silica, alumina, zirconia, titania, ceria, vanadia, carbon, heteropolyacids, silica-alumina, silica nitride, boron nitride, and mixtures thereof.

* * * * *